(12) United States Patent
Nigam et al.

(10) Patent No.: US 7,736,351 B2
(45) Date of Patent: Jun. 15, 2010

(54) SIMPLE DISPOSABLE ABSORBENT ARTICLE

(75) Inventors: Pankaj Nigam, Mason, OH (US); Gary Dean LaVon, Liberty Township, OH (US); Theodora Beck, Colerain Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 475 days.

(21) Appl. No.: 10/770,043

(22) Filed: Feb. 2, 2004

(65) Prior Publication Data

US 2005/0171499 A1 Aug. 4, 2005

(51) Int. Cl.
*A61F 13/15* (2006.01)

(52) U.S. Cl. ............... 604/385.28; 604/385.16; 604/385.21; 604/385.22; 604/385.24; 604/385.25; 604/385.29; 604/389

(58) Field of Classification Search ............ 604/385.28, 604/385.16, 385.21, 385.22, 385.24, 385.25, 604/385.29, 386, 389
See application file for complete search history.

(56) References Cited

U.S. PATENT DOCUMENTS

| | | |
|---|---|---|
| 1,733,997 A | 10/1929 | Marr |
| 1,734,499 A | 11/1929 | Marinsky |
| 1,989,283 A | 1/1935 | Limacher |
| 2,058,509 A | 10/1936 | Rose |
| 2,271,676 A | 2/1942 | Bjornbak |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,788,786 A | 4/1957 | Dexter |
| 2,798,489 A | 7/1957 | Behrman |

(Continued)

FOREIGN PATENT DOCUMENTS

| | | |
|---|---|---|
| DE | 19732499 | 2/1999 |
| EP | 0 206 208 A1 | 12/1986 |
| EP | 374542 | 6/1990 |
| EP | 0 403 832 A1 | 12/1990 |
| EP | 0 761 194 A2 | 3/1997 |

(Continued)

OTHER PUBLICATIONS

U.S. Appl. No. 11/133,818, filed May 20, 2005, LaVon et al.

(Continued)

*Primary Examiner*—Jacqueline F. Stephens
(74) *Attorney, Agent, or Firm*—Richard L. Alexander

(57) ABSTRACT

A simple disposable absorbent article including a chassis and an absorbent assembly. The chassis includes a water-impermeable sheet folded laterally inward at both of its side edges to form opposing side flaps. Each side flap is attached to the interior surface of the chassis adjacent to its end edges. Each side flap has a longitudinally extending elastic gathering member attached adjacent to its proximal edge. The absorbent assembly is smaller in width and in length than the chassis. The side edges and end edges of the absorbent assembly may be disposed proximally relative to the respective side edges and end edges of the chassis. The absorbent assembly includes an absorbent core that may contain superabsorbent particles, which may be contained inside pockets. The chassis may be extensible. The absorbent assembly may be attached in a cruciform pattern to the chassis to allow portions of the chassis to extend laterally.

31 Claims, 18 Drawing Sheets

U.S. PATENT DOCUMENTS

| | | |
|---|---|---|
| 2,807,263 A | 9/1957 | Newton |
| 2,830,589 A | 4/1958 | Doner |
| 2,890,700 A | 6/1959 | Longberg-Helm |
| 2,890,701 A | 6/1959 | Weinman |
| 2,898,912 A | 8/1959 | Adams |
| 2,931,361 A | 4/1960 | Sostsrin |
| 2,977,957 A | 4/1961 | Clyne |
| 3,180,335 A | 4/1965 | Duncan et al |
| 3,207,158 A | 9/1965 | Kazuko et al. |
| 3,386,442 A | 6/1968 | Sabee |
| 3,561,446 A | 2/1971 | Jones |
| 3,572,342 A | 3/1971 | Lindquist et al. |
| 3,572,432 A | 3/1971 | Burton |
| 3,578,155 A | 5/1971 | Small et al. |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,688,767 A | 9/1972 | Goldstein |
| 3,710,797 A | 1/1973 | Marsen |
| 3,731,688 A | 5/1973 | Litt et al |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand et al |
| 3,828,784 A | 10/1974 | Sabee |
| 3,840,418 A | 10/1974 | Sabee |
| 3,847,702 A | 11/1974 | Jones |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al |
| 3,882,870 A | 5/1975 | Hathaway |
| 3,884,234 A | 5/1975 | Taylor |
| 3,900,032 A | 8/1975 | Heurlen |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,074,508 A | 2/1978 | Reid |
| 4,084,592 A | 4/1978 | Tritsch |
| 4,100,922 A | 7/1978 | Hernandez |
| 4,257,418 A | 3/1981 | Hessner |
| 4,296,750 A | 10/1981 | Woon et al. |
| 4,315,508 A | 2/1982 | Bolick |
| 4,324,246 A | 4/1982 | Mullane et al. |
| 4,341,216 A * | 7/1982 | Obenour .................... 604/370 |
| 4,342,314 A | 8/1982 | Radel et al. |
| 4,388,075 A | 6/1983 | Mesek et al. |
| 4,461,621 A | 7/1984 | Karami et al. |
| 4,463,045 A | 7/1984 | Ahr et al. |
| 4,475,912 A | 10/1984 | Coates |
| 4,490,148 A | 12/1984 | Beckeström |
| 4,527,990 A | 7/1985 | Sigl |
| 4,578,072 A | 3/1986 | Lancaster |
| 4,578,702 A | 3/1986 | Campbell |
| 4,585,450 A | 4/1986 | Rosch et al. |
| 4,589,878 A | 5/1986 | Mitrani |
| 4,601,717 A | 7/1986 | Blevins |
| 4,606,964 A | 8/1986 | Wideman |
| 4,610,678 A | 9/1986 | Weisman et al. |
| 4,623,342 A | 11/1986 | Ito et al. |
| 4,636,207 A | 1/1987 | Buell |
| 4,641,381 A | 2/1987 | Heran et al. |
| 4,670,011 A | 6/1987 | Mesek |
| 4,670,012 A | 6/1987 | Johnson |
| 4,680,030 A | 7/1987 | Coates et al. |
| 4,681,579 A | 7/1987 | Toussant et al. |
| 4,681,581 A | 7/1987 | Coates |
| 4,690,680 A * | 9/1987 | Higgins ...................... 604/386 |
| 4,695,278 A | 9/1987 | Lawson |
| 4,704,115 A | 11/1987 | Buell |
| 4,704,116 A | 11/1987 | Enloe |
| 4,731,066 A | 3/1988 | Korpman |
| 4,731,070 A | 3/1988 | Koci |
| 4,747,846 A | 5/1988 | Boland et al. |
| 4,784,892 A * | 11/1988 | Storey et al. ................. 428/172 |
| 4,787,896 A | 11/1988 | Houghton et al. |
| 4,795,454 A | 1/1989 | Dragoo |
| 4,802,884 A | 2/1989 | Froidh |
| 4,808,176 A | 2/1989 | Kielpikowski |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,846,825 A | 7/1989 | Enloe et al. |
| 4,861,652 A | 8/1989 | Lippert et al. |
| 4,888,231 A | 12/1989 | Angstadt |
| 4,892,528 A | 1/1990 | Suzuki et al. |
| 4,892,536 A | 1/1990 | DesMarais et al. |
| 4,900,317 A | 2/1990 | Buell |
| 4,904,251 A | 2/1990 | Igaue et al. |
| 4,909,802 A | 3/1990 | Ahr et al. |
| 4,909,803 A | 3/1990 | Aziz et al. |
| 4,940,463 A | 7/1990 | Leathers et al. |
| 4,940,464 A | 7/1990 | Van Gompel et al. |
| 4,950,264 A | 8/1990 | Osborn |
| 4,963,140 A | 10/1990 | Robertson et al. |
| 4,968,313 A | 11/1990 | Sabee |
| 4,990,147 A | 2/1991 | Freeland |
| 5,006,394 A | 4/1991 | Baird |
| 5,019,072 A | 5/1991 | Polski |
| 5,021,051 A | 6/1991 | Hiuke |
| 5,032,120 A | 7/1991 | Freeland et al. |
| 5,034,008 A | 7/1991 | Breitkopf |
| 5,037,416 A | 8/1991 | Allen et al. |
| 5,071,414 A | 12/1991 | Elliott |
| 5,085,654 A * | 2/1992 | Buell ......................... 604/370 |
| 5,092,861 A | 3/1992 | Nomura et al. |
| 5,114,420 A | 5/1992 | Igaue et al. |
| 5,135,522 A | 8/1992 | Fahrenkrug et al. |
| D329,697 S | 9/1992 | Fahrenkrug et al. |
| 5,151,092 A | 9/1992 | Buell et al. |
| 5,190,606 A | 3/1993 | Merkatoris et al. |
| 5,204,997 A | 4/1993 | Suzuki et al. |
| 5,221,274 A | 6/1993 | Buell et al. |
| 5,235,515 A | 8/1993 | Ungpiyakul et al. |
| 5,246,431 A * | 9/1993 | Minetola et al. ......... 604/385.28 |
| 5,246,432 A | 9/1993 | Suzuki et al. |
| 5,246,433 A | 9/1993 | Hasse et al. |
| 5,260,345 A | 11/1993 | DesMarais et al. |
| 5,269,775 A | 12/1993 | Freeland et al. |
| 5,312,386 A | 5/1994 | Correa et al. |
| 5,358,500 A | 10/1994 | LaVon et al. |
| 5,366,782 A | 11/1994 | Curro et al. |
| 5,387,209 A | 2/1995 | Yamamoto et al. |
| 5,397,316 A | 3/1995 | LaVon et al. |
| H1440 H | 5/1995 | New et al. |
| 5,415,644 A | 5/1995 | Enloe |
| 5,476,458 A | 12/1995 | Glaug et al. |
| 5,507,895 A | 4/1996 | Suekane |
| 5,518,801 A | 5/1996 | Chappell et al. |

| | | |
|---|---|---|
| 5,531,730 A | 7/1996 | Dreier |
| 5,542,943 A | 8/1996 | Sageser |
| 5,549,592 A | 8/1996 | Fries et al. |
| 5,549,593 A | 8/1996 | Ygge et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,584,829 A | 12/1996 | Lavash et al. |
| 5,607,416 A | 3/1997 | Yamamoto et al. |
| 5,607,537 A | 3/1997 | Johnson et al. |
| 5,607,760 A | 3/1997 | Roe |
| 5,609,587 A | 3/1997 | Roe |
| 5,613,959 A | 3/1997 | Roessler et al. |
| 5,622,589 A | 4/1997 | Johnson et al. |
| 5,624,424 A | 4/1997 | Saisaka et al. |
| 5,625,222 A | 4/1997 | Yoneda et al. |
| 5,626,571 A | 5/1997 | Young et al. |
| 5,635,191 A | 6/1997 | Roe et al. |
| 5,643,243 A | 7/1997 | Klemp |
| 5,643,588 A | 7/1997 | Roe et al. |
| H1674 H | 8/1997 | Ames et al. |
| 5,662,638 A | 9/1997 | Johnson et al. |
| 5,674,215 A | 10/1997 | Ronnberg |
| 5,685,874 A | 11/1997 | Buell et al. |
| 5,691,035 A | 11/1997 | Chappell et al. |
| 5,691,036 A | 11/1997 | Lin et al. |
| 5,695,488 A | 12/1997 | Sosalla |
| 5,723,087 A | 3/1998 | Chappell et al. |
| 5,733,275 A | 3/1998 | Davis et al. |
| 5,749,866 A | 5/1998 | Roe et al. |
| 5,752,947 A | 5/1998 | Awolin |
| 5,766,389 A | 6/1998 | Brandon et al. |
| 5,772,825 A | 6/1998 | Schmitz |
| 5,776,121 A | 7/1998 | Roe et al. |
| 5,779,831 A | 7/1998 | Schmitz |
| 5,797,894 A | 8/1998 | Cadieux et al. |
| 5,810,800 A | 9/1998 | Hunter et al. |
| 5,814,035 A | 9/1998 | Gryskiewicz et al. |
| 5,820,618 A | 10/1998 | Roberts et al. |
| 5,846,232 A | 12/1998 | Serbiak et al. |
| 5,851,204 A | 12/1998 | Mizutani |
| 5,858,013 A | 1/1999 | Kling |
| 5,865,823 A | 2/1999 | Curro |
| 5,873,868 A | 2/1999 | Nakahata |
| 5,876,391 A | 3/1999 | Roe et al. |
| 5,891,544 A | 4/1999 | Chappell et al. |
| 5,897,545 A | 4/1999 | Kline et al. |
| 5,904,673 A | 5/1999 | Roe et al. |
| 5,931,825 A | 8/1999 | Kuen et al. |
| 5,947,949 A | 9/1999 | Inoue et al. |
| 5,951,536 A | 9/1999 | Osborn, III et al. |
| 5,957,908 A | 9/1999 | Kline et al. |
| 5,968,029 A | 10/1999 | Chappell et al. |
| 5,989,236 A | 11/1999 | Roe et al. |
| 6,004,306 A | 12/1999 | Robles et al. |
| 6,022,430 A | 2/2000 | Blenke et al. |
| 6,022,431 A | 2/2000 | Blenke et al. |
| 6,042,673 A | 3/2000 | Johnson et al. |
| 6,102,892 A | 8/2000 | Putzer et al. |
| 6,107,537 A | 8/2000 | Elder et al. |
| 6,110,157 A | 8/2000 | Schmidt |
| 6,117,121 A | 9/2000 | Faulks et al. |
| 6,117,803 A | 9/2000 | Morman et al. |
| 6,120,486 A | 9/2000 | Toyoda et al. |
| 6,120,487 A | 9/2000 | Ashton |
| 6,120,489 A | 9/2000 | Johnson et al. |
| 6,120,866 A | 9/2000 | Arakawa et al. |
| 8,120,486 | 9/2000 | Toyoda et al. |
| 6,129,720 A | 10/2000 | Blenke et al. |
| 6,156,023 A | 12/2000 | Yoshioka |
| 6,156,424 A | 12/2000 | Taylor |
| 6,165,160 A | 12/2000 | Suzuki et al. |
| 6,174,302 B1 | 1/2001 | Kumasaka |
| 6,177,607 B1 | 1/2001 | Blaney et al. |
| 6,186,996 B1 | 2/2001 | Martin |
| 6,210,386 B1 | 4/2001 | Inoue |
| 6,210,390 B1 | 4/2001 | Karlsson |
| 6,238,380 B1 | 5/2001 | Sasaki |
| 6,241,716 B1 | 6/2001 | Ronnberg |
| 6,254,294 B1 | 7/2001 | Muhar |
| 6,306,122 B1 | 10/2001 | Narawa et al. |
| 6,322,552 B1 | 11/2001 | Blenke et al. |
| 6,325,787 B1 | 12/2001 | Roe et al. |
| 6,334,858 B1 | 1/2002 | Ronnberg et al. |
| 6,336,922 B1 | 1/2002 | Van Gompel et al. |
| 6,350,332 B1 | 2/2002 | Thomas et al. |
| 6,402,729 B1 | 6/2002 | Boberg et al. |
| 6,402,731 B1 | 6/2002 | Suprise et al. |
| 6,410,820 B1 | 6/2002 | McFall et al. |
| 6,413,249 B1 | 7/2002 | Turi et al. |
| 6,419,667 B1 | 7/2002 | Avalon et al. |
| 6,432,098 B1 | 8/2002 | Kline et al. |
| 6,432,099 B2 | 8/2002 | Ronnberg |
| 6,443,933 B1 | 9/2002 | Suzuki et al. |
| 6,461,342 B2 | 10/2002 | Tanji et al. |
| 6,475,201 B2 | 11/2002 | Saito et al. |
| 6,494,872 B1 | 12/2002 | Suzuki et al. |
| 6,494,873 B2 | 12/2002 | Karlsson et al. |
| 6,520,947 B1 | 2/2003 | Tilly et al. |
| 6,524,294 B1 | 2/2003 | Hilston et al. |
| 6,585,713 B1 | 7/2003 | LaMahieu et al. |
| 6,605,070 B2 | 8/2003 | Ludwig et al. |
| 6,648,869 B1 | 11/2003 | Gillies et al. |
| 6,648,870 B2 | 11/2003 | Itoh et al. |
| 6,648,871 B2 | 11/2003 | Kusibojoska et al. |
| 6,682,515 B1 | 1/2004 | Mizutani et al. |
| 6,689,115 B1 | 2/2004 | Popp et al. |
| 6,726,792 B1 | 4/2004 | Johnson et al. |
| 6,818,083 B2 | 11/2004 | McAmish et al. |
| 6,880,211 B2 | 4/2005 | Jackson et al. |
| 6,923,797 B2 | 8/2005 | Shinohara et al. |
| 6,962,578 B1 | 11/2005 | LaVon |
| 6,972,010 B2 | 12/2005 | Pesce et al. |
| 7,014,632 B2 | 3/2006 | Takino et al. |
| 7,037,299 B2 | 5/2006 | Turi et al. |
| 7,048,726 B2 | 5/2006 | Kusagawa et al. |
| 7,160,281 B2 | 1/2007 | Leminh et al. |
| 2002/0045881 A1 | 4/2002 | Kusibojoska et al. |
| 2002/0087139 A1 | 7/2002 | Popp et al. |
| 2002/0151861 A1 | 10/2002 | Klemp et al. |
| 2002/0173767 A1* | 11/2002 | Popp et al. .................. 604/387 |
| 2003/0088223 A1 | 5/2003 | Vogt et al. |
| 2003/0144644 A1 | 7/2003 | Murai et al. |
| 2003/0148694 A1 | 8/2003 | Ghiam |
| 2003/0233082 A1 | 12/2003 | Kline et al. |
| 2004/0022998 A1 | 2/2004 | Miyamoto et al. |
| 2004/0082928 A1 | 4/2004 | Pesce et al. |
| 2004/0122411 A1 | 6/2004 | Hancock-Cooke |
| 2004/0147890 A1 | 7/2004 | Nakahata et al. |
| 2004/0162536 A1 | 8/2004 | Becker et al. |
| 2004/0167486 A1 | 8/2004 | Busam et al. |
| 2004/0225271 A1 | 11/2004 | Datta et al. |
| 2004/0236299 A1 | 11/2004 | Tsang et al. |
| 2004/0249355 A1 | 12/2004 | Tanio et al. |
| 2005/0004543 A1 | 1/2005 | Schroer et al. |
| 2005/0004548 A1 | 1/2005 | Otsubo et al. |
| 2005/0038401 A1 | 2/2005 | Suzuki et al. |
| 2005/0085784 A1 | 4/2005 | LeMinh et al. |
| 2005/0203475 A1 | 9/2005 | LaVon et al. |
| 2005/0288645 A1 | 12/2005 | LaVon |
| 2005/0288646 A1 | 12/2005 | LaVon |

2006/0264860 A1 11/2006 Beck

FOREIGN PATENT DOCUMENTS

| | | |
|---|---|---|
| EP | 0 893 115 A2 | 1/1999 |
| EP | 0 951 890 A2 | 1/1999 |
| EP | 0 916 327 A1 | 5/1999 |
| EP | 0951890 B1 | 10/1999 |
| EP | 0 793 469 B1 | 6/2002 |
| EP | 1 224 922 A2 | 7/2002 |
| EP | 1 447 066 A1 | 8/2004 |
| EP | 1 447 067 A1 | 8/2004 |
| ES | 2 213 491 A1 | 8/2004 |
| FR | 2 566 631 A1 | 1/1986 |
| FR | 2 612 770 A1 | 9/1988 |
| FR | 2 810 234 A1 | 12/2001 |
| GB | 1 307 441 | 2/1973 |
| GB | 1 513 055 | 6/1978 |
| GB | 2 101 468 A | 1/1983 |
| GB | 2 262 873 A | 7/1993 |
| JP | 04 122256 A | 4/1992 |
| JP | 11318980 | 11/1999 |
| JP | 2000-238161 | 9/2000 |
| JP | 2001-198157 | 7/2001 |
| JP | 2002-165832 | 6/2002 |
| WO | WO 95/14453 | 6/1995 |
| WO | WO 95/16746 | 6/1995 |
| WO | WO 95/19753 | 7/1995 |
| WO | WO 95/29657 A1 | 11/1995 |
| WO | WO 98/16179 A1 | 4/1998 |
| WO | WO 99/13813 | 3/1999 |
| WO | WO 99/13813 A1 | 3/1999 |
| WO | WO 03/009794 A2 | 2/2003 |
| WO | WO 2004/105664 | 12/2004 |
| WO | WO 2005/087164 A1 | 9/2005 |
| WO | WO 2007/000315 A1 | 1/2007 |

OTHER PUBLICATIONS

U.S. Appl. No. 11/135,689, filed May 24, 2005, LaVon.
U.S. Appl. No. 11/140,888, filed May 31, 2005, LaVon et al.
U.S. Appl. No. 11/197,197, filed Aug. 4, 2005, LaVon et al.
U.S. Appl. No. 11/210,345, filed Aug. 24, 2005, LaVon et al.
U.S. Appl. No. 11/286,934, filed Nov. 23, 2005, LaVon et al.
U.S. Appl. No. 10/770,043, Feb. 2, 2004, Notice of Allowance dated Oct. 5, 2009.
U.S. Appl. No. 10/770,043, Feb. 2, 2004, Office Action dated Jun. 16, 2009.
U.S. Appl. No. 10/770,043, Feb. 2, 2004, Office Action dated Feb. 18, 2009.
U.S. Appl. No. 10/770,043, Feb. 2, 2004, Office Action dated Jan. 11, 2008.
U.S. Appl. No. 10/770,043, Feb. 2, 2004, Office Action dated Jul. 17, 2007.
U.S. Appl. No. 10/770,043, Feb. 2, 2004, Office Action dated Mar. 9, 2007.
U.S. Appl. No. 10/770,043, Feb. 2, 2004, Office Action dated Sep. 13, 2006.
U.S. Appl. No. 10/770,043, Feb. 2, 2004, Office Action dated Mar. 23, 2006.
U.S. Appl. No. 110/799,947, Mar. 10, 2005, Patent Issuance dated Jan. 15, 2008.
U.S. Appl. No. 110/799,947, Mar. 10, 2005, Notice of Allowance dated Oct. 2, 2007.
U.S. Appl. No. 110/799,947, Mar. 10, 2005, Office Action dated Jul. 20, 2007.
U.S. Appl. No. 110/799,947, Mar. 10, 2005, Office Action dated Apr. 11, 2007.
U.S. Appl. No. 110/799,947, Mar. 10, 2005, Office Action dated Oct. 16, 2006.
U.S. Appl. No. 110/799,947, Mar. 10, 2005, Office Action dated Jul. 13, 2006.
U.S. Appl. No. 110/799,947, Mar. 10, 2005, Office Action dated Mar. 16, 2006.
U.S. Appl. No. 110/799,947, Mar. 10, 2005, Office Action dated Oct. 4, 2005.
U.S. Appl. No. 10/880,135, Nov. 8, 2005, Patent Issuance dated Nov. 8, 2005.
U.S. Appl. No. 10/880,135, Nov. 8, 2005, Notice of Allowance dated Jun. 17, 2005.
U.S. Appl. No. 10/880,135, Nov. 8, 2005, Office Action dated Nov. 12, 2004.
U.S. Appl. No. 11/172,191, Jun. 29, 2004, Patent Issuance dated May 27, 2008.
U.S. Appl. No. 11/172,191, Jun. 29, 2004, Notice of Allowance dated Aug. 7, 2007.
U.S. Appl. No. 11/172,191, Jun. 29, 2004, Office Action dated Feb. 16, 2007.
U.S. Appl. No. 11/172,191, Jun. 29, 2004, Office Action dated Aug. 10, 2006.
U.S. Appl. No. 11/131,799, May 18, 2005, Office Action dated Aug. 20, 2009.
U.S. Appl. No. 11/131,799, May 18, 2005, Office Action dated Feb. 4, 2009.
U.S. Appl. No. 11/131,799, May 18, 2005, Office Action dated Aug. 6, 2008.
U.S. Appl. No. 11/131,799, May 18, 2005, Office Action dated Oct. 2, 2007.
U.S. Appl. No. 11/133,818, May 20, 2005, Office Action dated Nov. 9, 2009.
U.S. Appl. No. 11/133,818, May 20, 2005, Office Action dated Apr. 1, 2009.
U.S. Appl. No. 11/133,818, May 20, 2005, Office Action dated Dec. 9, 2008.
U.S. Appl. No. 11/133,818, May 20, 2005, Office Action dated Jun. 18, 2008.
U.S. Appl. No. 11/133,818, May 20, 2005, Office Action dated Dec. 31, 2007.
U.S. Appl. No. 11/133,818, May 20, 2005, Office Action dated Jun. 26, 2007.
U.S. Appl. No. 11/135,689, May 25, 2005, Office Action dated Sep. 22, 2009.
U.S. Appl. No. 11/135,689, May 25, 2005, Office Action dated Feb. 24, 2009.
U.S. Appl. No. 11/135,689, May 25, 2005, Office Action dated Oct. 16, 2008.
U.S. Appl. No. 11/135,689, May 25, 2005, Office Action dated Apr. 3, 2008.
U.S. Appl. No. 11/135,689, May 25, 2005, Office Action dated Oct. 9, 2007.
U.S. Appl. No. 11/135,689, May 25, 2005, Office Action dated Jun. 4, 2007.
U.S. Appl. No. 11/135,689, May 25, 2005, Office Action dated Oct. 6, 2006.
U.S. Appl. No. 11/140,888, May 20, 2005, Office Action dated Dec. 17, 2009.
U.S. Appl. No. 11/140,888, May 20, 2005, Office Action dated Jul. 21, 2009.
U.S. Appl. No. 11/140,888, May 20, 2005, Office Action dated Dec. 30, 2008.
U.S. Appl. No. 11/140,888, May 20, 2005 Office Action dated Oct. 10, 2008.
U.S. Appl. No. 11/140,888, May 20, 2005 Office Action dated Mar. 28, 2008.
U.S. Appl. No. 11/140,888 May 20, 2005 Office Action dated Dec. 13, 2007.
U.S. Appl. No. 11/140,888, May 20, 2005 Office Action dated Jun. 27, 2007.
U.S. Appl. No. 11/159,916, Jun. 23, 2005, Patent Issuance dated Nov. 17, 2009.
U.S. Appl. No. 11/159,916, Jun. 23, 2005, Notice of Allowance dated Sep. 17, 2009.
U.S. Appl. No. 11/159,916, Jun. 23, 2005, Notice of Allowance dated Mar. 6, 2009.
U.S. Appl. No. 11/159,916, Jun. 23, 2005, Office Action dated Apr. 18, 2008.

U.S. Appl. No. 11/159,916, Jun. 23, 2005, Office Action dated Nov. 1, 2007.
U.S. Appl. No. 11/197,197, Aug. 4, 2005, Office Action dated Aug. 10, 2009.
U.S. Appl. No. 11/197,197, Aug. 4, 2005, Office Action dated May 7, 2008.
U.S. Appl. No. 11/197,197, Aug. 4, 2005, Office Action dated Nov. 7, 2007.
U.S. Appl. No. 11/197,197, Aug. 4, 2005, Office Action dated Jul. 6, 2007.
U.S. Appl. No. 11/197,197, Aug. 4, 2005, Office Action dated Apr. 12, 2007.
U.S. Appl. No. 11/197,197, Aug. 4, 2005 Office Action dated Sep. 27, 2006.
U.S. Appl. No. 11/210,345, Aug. 24, 2005, Office Action dated Sep. 28, 2009.
U.S. Appl. No. 11/210,345, Aug. 24, 2005 Office Action dated Jun. 23, 2009.
U.S. Appl. No. 11/210,345, Aug. 24, 2005, Office Action dated Jan. 9, 2009.
U.S. Appl. No. 11/210,345, Aug. 24, 2005 Office Action dated Sep. 10, 2008.
U.S. Appl. No. 11/210,345, Aug. 24, 2005, Office Action dated Apr. 8, 2008.
U.S. Appl. No. 11/210,345, Aug. 24, 2005, Office Action dated Oct. 18, 2007.
U.S. Appl. No. 11/210,345, Aug. 24, 2005, Office Action dated Feb. 12, 2007.
U.S. Appl. No. 11/224,462, Sep. 12, 2005, Office Action dated May 5, 2009.
U.S. Appl. No. 11/224,462, Sep. 12, 2005, Office Action dated Oct. 23, 2009.
U.S. Appl. No. 11/224,462, Sep. 12, 2005, Office Action dated Dec. 12, 2008.
U.S. Appl. No. 11/224,462, Sep. 12, 2005, Office Action dated May 28, 2008.
U.S. Appl. No. 11/224,462, Sep. 12, 2005, Office Action dated Nov. 29, 2007.
U.S. Appl. No. 11/224,462, Sep. 12, 2005, Office Action dated Jul. 10, 2007.
U.S. Appl. No. 11/231,512, Sep. 21, 2005, Office Action dated Jul. 22, 2009.
U.S. Appl. No. 11/231,512, Sep. 21, 2005, Office Action dated Jan. 6, 2009.
U.S. Appl. No. 11/231,512, Sep. 21, 2005, Office Action dated Jun. 27, 2008.
U.S. Appl. No. 11/231,500, Sep. 21, 2005, Office Action dated Sep. 28, 2009.
U.S. Appl. No. 11/231,500, Sep. 21, 2005, Office Action dated Jun. 24, 2009.
U.S. Appl. No. 11/231,500, Sep. 21, 2005, Office Action dated Jan. 8, 2009.
U.S. Appl. No. 11/231,500, Sep. 21, 2005, Office Action dated Sep. 22, 2008.
U.S. Appl. No. 11/231,500, Sep. 21, 2005, Office Action dated Mar. 4, 2008.
U.S. Appl. No. 11/231,500, Sep. 21, 2005, Office Action dated Aug. 22, 2007.
U.S. Appl. No. 11/231,500, Sep. 21, 2005, Office Action dated Jun. 8, 2006.
U.S. Appl. No. 11/286,934, Nov. 23, 2005, Office Action dated Jun. 23, 2009.
U.S. Appl. No. 11/286,934, Nov. 23, 2005, Office Action dated May 30, 2008.
U.S. Appl. No. 11/286,934, Nov. 23, 2005, Office Action dated Dec. 31, 2007.
U.S. Appl. No. 11/286,934, Nov. 23, 2005, Office Action dated Jun. 28, 2007.
U.S. Appl. No. 11/268,614, Nov. 23, 2005, Office Action dated Nov. 20, 2009.
U.S. Appl. No. 11/268,614, Nov. 23, 2005, Office Action dated Jun. 8, 2009.
U.S. Appl. No. 11/268,614, Nov. 23, 2005, Office Action dated Jan. 2, 2009.
U.S. Appl. No. 11/268,614, Nov. 23, 2005, Office Action dated Jun. 11, 2008.
U.S. Appl. No. 11/709,500, Feb. 27, 2007, Office Action dated Aug. 28, 2009.
U.S. Appl. No. 11/709,500, Feb. 27, 2007, Office Action dated Sep. 25, 2008.
U.S. Appl. No. 11/232,193, Sep. 21, 2005, Patent Issuance dated Jan. 22, 2008.
U.S. Appl. No. 11/232,193, Sep. 21, 2005, Notice of Allowance dated Aug. 28, 2007.
U.S. Appl. No. 11/232,193, Sep. 21, 2005, Office Action dated Jun. 7, 2006.
U.S. Appl. No. 11/713,906, Feb. 28, 2007, Office Action dated Sep. 15, 2009.
U.S. Appl. No. 11/713,906, Feb. 28, 2007, Office Action dated Apr. 13, 2009.
U.S. Appl. No. 11/713,906, Feb. 28, 2007, Office Action dated Jun. 26, 2008.

* cited by examiner

SIMPLE DISPOSABLE ABSORBENT ARTICLE

FIELD OF THE INVENTION

This invention relates to disposable absorbent articles such as disposable diapers and other articles intended for use on incontinent persons.

BACKGROUND OF THE INVENTION

Disposable absorbent articles are designed to absorb and contain bodily waste in order to prevent soiling of the body and clothing of the wearer, as well as bedding or other objects with which the wearer comes into contact.

As the usage of disposable absorbent articles has expanded, their complexity has increased with the incorporation of additional features serving to enhance their performance and appearance. The costs of the materials and the costs of the manufacturing processes have also increased in conjunction with the increase in complexity. As a result, the prices at which these articles are sold have risen to levels that many potential purchasers around the world cannot afford to pay. Thus, a need exists for a simple disposable absorbent article.

SUMMARY OF THE INVENTION

The present invention provides a simple disposable absorbent article including a chassis and an absorbent assembly. The chassis includes a water-impermeable sheet that may be folded laterally inward at both of its side edges to form opposing side flaps. Each side flap is attached to the interior surface of the chassis adjacent to its end edges. Each side flap has a longitudinally extending elastic gathering member attached adjacent to its proximal edge. The absorbent assembly is smaller in width and in length than the chassis. The side edges and end edges of the absorbent assembly may be disposed proximally relative to the respective side edges and end edges of the chassis. The absorbent assembly includes an absorbent core. The absorbent core may contain superabsorbent particles and these particles may be contained inside pockets. The chassis may include an extensible formed web material. The absorbent assembly may be attached in a cruciform pattern to the chassis to allow portions of the chassis to extend laterally.

BRIEF DESCRIPTION OF THE DRAWINGS

In the accompanying drawing figures, like reference numerals identify like elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description.

In FIG. 1, the interior portion of the diaper 20 that faces inwardly toward the wearer and contacts the wearer is shown facing the viewer.

In FIG. 10, the interior portion of the diaper 20 that faces inwardly toward the wearer and contacts the wearer is shown facing the viewer.

In FIG. 16, the interior portion of the diaper 20 that faces inwardly toward the wearer and contacts the wearer is shown facing upward.

In FIG. 21, the interior portion of the diaper 20 that faces inwardly toward the wearer and contacts the wearer is shown facing the viewer.

In FIG. 25, the interior portion of the diaper 20 that faces inwardly toward the wearer and contacts the wearer is shown facing the viewer.

In FIG. 29, the absorbent assembly 200 is shown separately from a chassis 100 to which it is attached in an exemplary diaper 20 and the interior portion of the absorbent assembly 200 that faces inwardly toward the wearer and contacts the wearer is shown facing the viewer.

DETAILED DESCRIPTION OF THE INVENTION

Definitions

Figure 1:
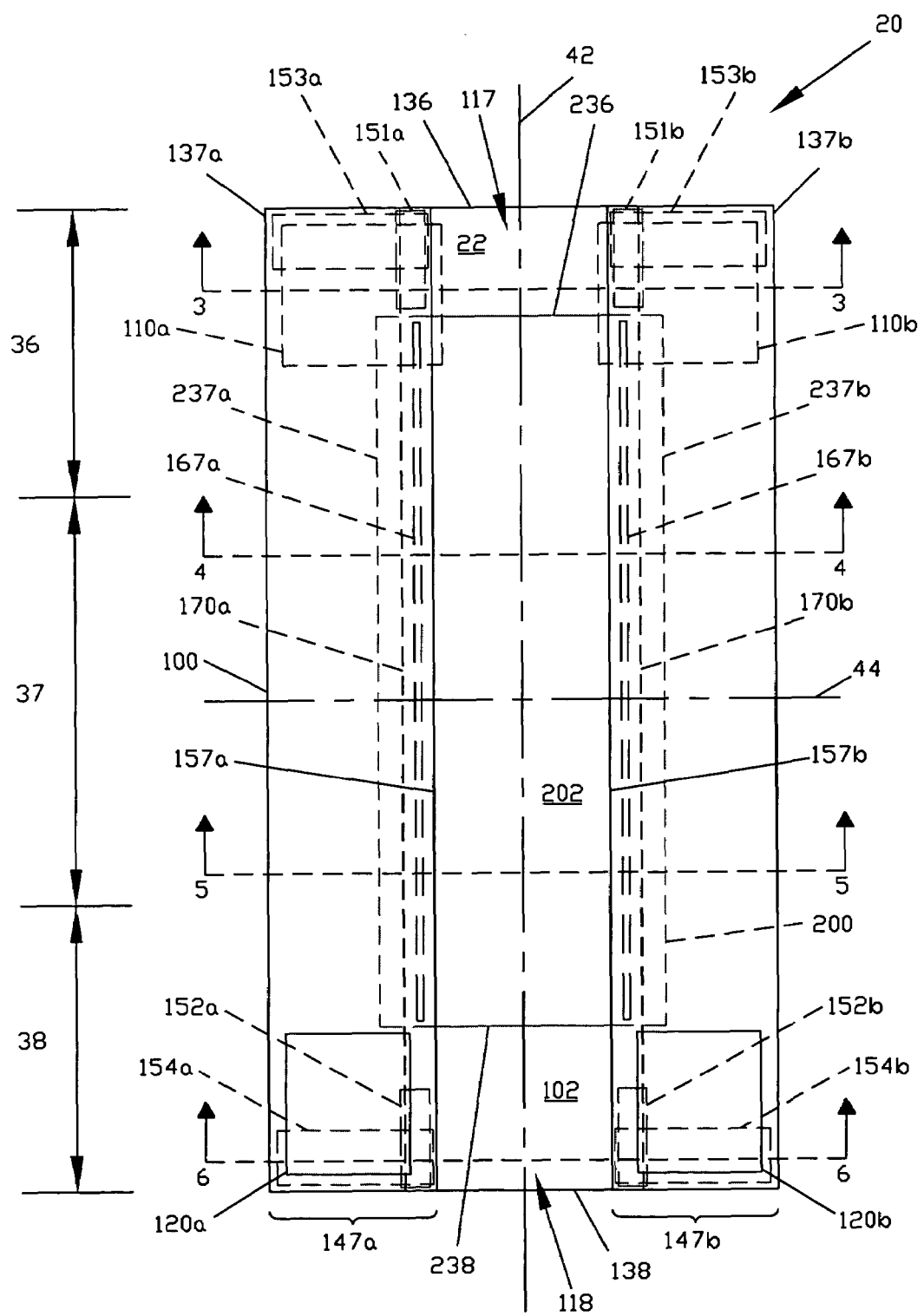
FIG. 1 is a plan view of an exemplary disposable absorbent article in the form of a diaper 20, which is shown in its flat, uncontracted state, i.e., without the contraction induced by elastic members.

In this description, the following terms have the following meanings:

The term "absorbent article" refers to a device that absorbs and contains liquid, and more specifically, refers to a device that is placed against or in proximity to the body of the wearer to absorb and contain the various exudates discharged from the body.

The term "diaper" refers to an absorbent article that is generally worn by infants and incontinent persons about the lower torso so as to encircle the waist and the legs of the wearer and that is specifically adapted to receive and contain urinary and fecal waste.

The term "disposable" refers to the nature of absorbent articles that generally are not intended to be laundered or otherwise restored or reused as an absorbent article, i.e., they are intended to be discarded after a single use and, preferably, to be recycled, composted or otherwise disposed of in an environmentally compatible manner.

The term "longitudinal" refers to a direction running from a waist edge to an opposing waist edge of the article and generally parallel to the maximum linear dimension of the article. Directions within ±45° of the longitudinal direction are considered to be "longitudinal".

The term "lateral" refers to a direction running from a side edge to an opposing side edge of the article and generally at a right angle to the longitudinal direction. Directions within ±45° of the lateral direction are considered to be "lateral".

The term "disposed" refers to an element being attached and positioned in a particular place or position in a unitary structure with other elements.

The term "attached" refers to elements being connected or united by fastening, adhering, bonding, etc. by any method suitable for the elements being attached together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently.

The term "cohesive" refers to the property of a material that sticks to itself but does not to any significant degree stick to other materials.

The terms "water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water to pass through its thickness in the absence of a forcing pressure. Conversely, the term "water-impermeable" refers to a layer or a layered structure through the thickness of which liquid water cannot pass in the absence of a forcing pressure. A layer or a layered structure that is water-impermeable according to this definition may be permeable to water vapor, i.e., may be "vapor-permeable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

The terms "proximal" and "distal" refer respectively to the location of an element near to or far from the center of a structure, e.g., the proximal edge of a longitudinally extending element is located nearer to the longitudinal axis than the distal edge of the same element is located relative to the same longitudinal axis.

Description of Exemplary Diaper Embodiment

As shown in FIG. 1, FIG. 2, FIG. 3, FIG. 4, FIG. 5, and FIG. 6, one end portion of the exemplary diaper 20 is configured as a front waist region 36. The longitudinally opposing end portion of the diaper 20 is configured as a back waist region 38. An intermediate portion of the diaper 20 extending longitudinally between the front waist region 36 and the back waist region 38 is configured as a crotch region 37.

The basic structure of the diaper 20 includes a chassis 100. The chassis 100 has a laterally extending front waist edge 136 in the front waist region 36 and a longitudinally opposing and laterally extending back waist edge 138 in the back waist region 38. The chassis 100 has a longitudinally extending left side edge 137a and a laterally opposing and longitudinally extending right side edge 137b, both chassis side edges extending longitudinally between the front waist edge 136 and the back waist edge 138. The chassis 100 has an interior surface 102 and an exterior surface 104. The chassis 100 also has a longitudinal axis 42 and a lateral axis 44. The longitudinal axis 42 extends through the midpoint of the front waist edge 136 and through the midpoint of the back waist edge 138 of the chassis 100. The lateral axis 44 extends through the midpoint of the left side edge 137*a* and through the midpoint of the right side edge 137*b* of the chassis 100. The exemplary chassis 100 shown in FIG. 1 additionally has longitudinally extending and laterally opposing side flaps 147*a* and 147*b* that are described in more detail below.

The basic structure of the diaper 20 also includes an absorbent assembly 200 that is attached to the chassis 100. The absorbent assembly 200 has a laterally extending front edge 236 in the front waist region 36 and a longitudinally opposing and laterally extending back edge 238 in the back waist region 38. The absorbent assembly 200 has a longitudinally extending left side edge 237*a* and a laterally opposing and longitudinally extending right side edge 237*b*, both absorbent assembly side edges extending longitudinally between the front edge 236 and the back edge 238. The absorbent assembly 200 has an interior surface 202 and an exterior surface 204. The absorbent assembly 200 may be disposed symmetrically with respect to either or both of the longitudinal axis 42 and the lateral axis 44. Alternatively, the absorbent assembly 200 may be disposed asymmetrically with respect to either or both of the longitudinal axis 42 and the lateral axis 44. For example, the absorbent assembly 200 shown in FIG. 1 is disposed symmetrically with respect to the longitudinal axis 42 and asymmetrically with respect to the lateral axis 44. In particular, the absorbent assembly 200 shown in FIG. 1 is disposed asymmetrically toward the front waist region 36.

The respective front edge 236, back edge 238, left side edge 237*a*, and right side edge 237*b* of the absorbent assembly 200 may lie inward of the respective front waist edge 136, back waist edge 138, left side edge 137*a*, and right side edge 137*b* of the chassis 100, as in the exemplary diaper 20 shown in FIG. 1. Such a configuration in which one or more of the edges of the absorbent assembly 200 lies inward of the corresponding edges of the chassis 100 may be desirable, for example, in order to allow the relatively more flexible layer or layers adjacent to the edges of the chassis to conform to the body of the wearer and thereby form effective gasket-like seals against the skin of the wearer without being constrained by a relatively thicker and relatively less flexible absorbent assembly. Alternatively, one or more of the edges of the absorbent assembly 200 may coincide with the corresponding edge or edges of the chassis 100.

Figure 7:
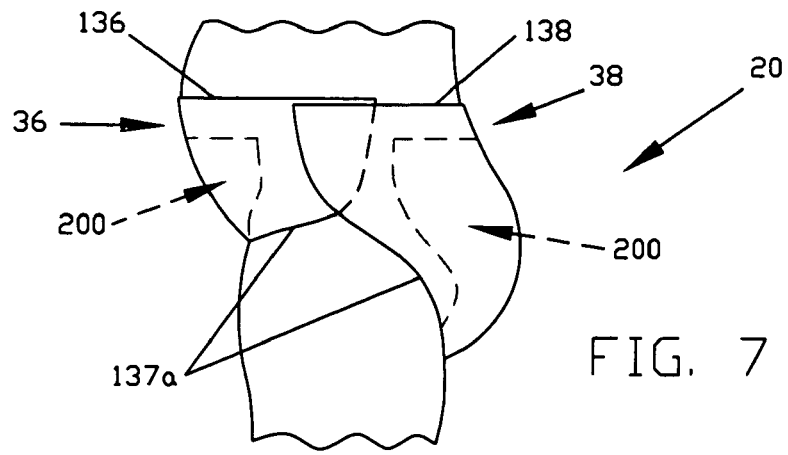
FIG. 7 is a simplified side elevation view of an exemplary diaper 20 being worn about a lower torso of a wearer.
Figure 8:
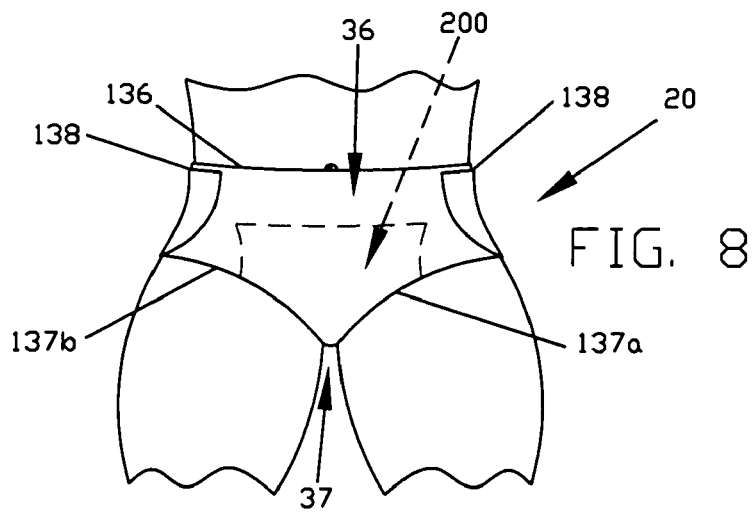
FIG. 8 is a front elevation view of the diaper 20 of FIG. 7 being worn about the lower torso of the wearer.
Figure 9:
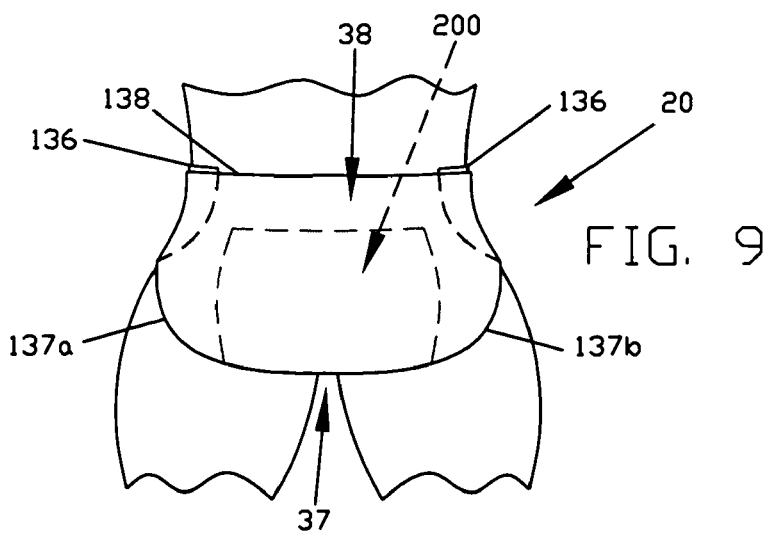
FIG. 9 is a back elevation view of the diaper 20 of FIG. 7 being worn about the lower torso of the wearer.
Figure 10:
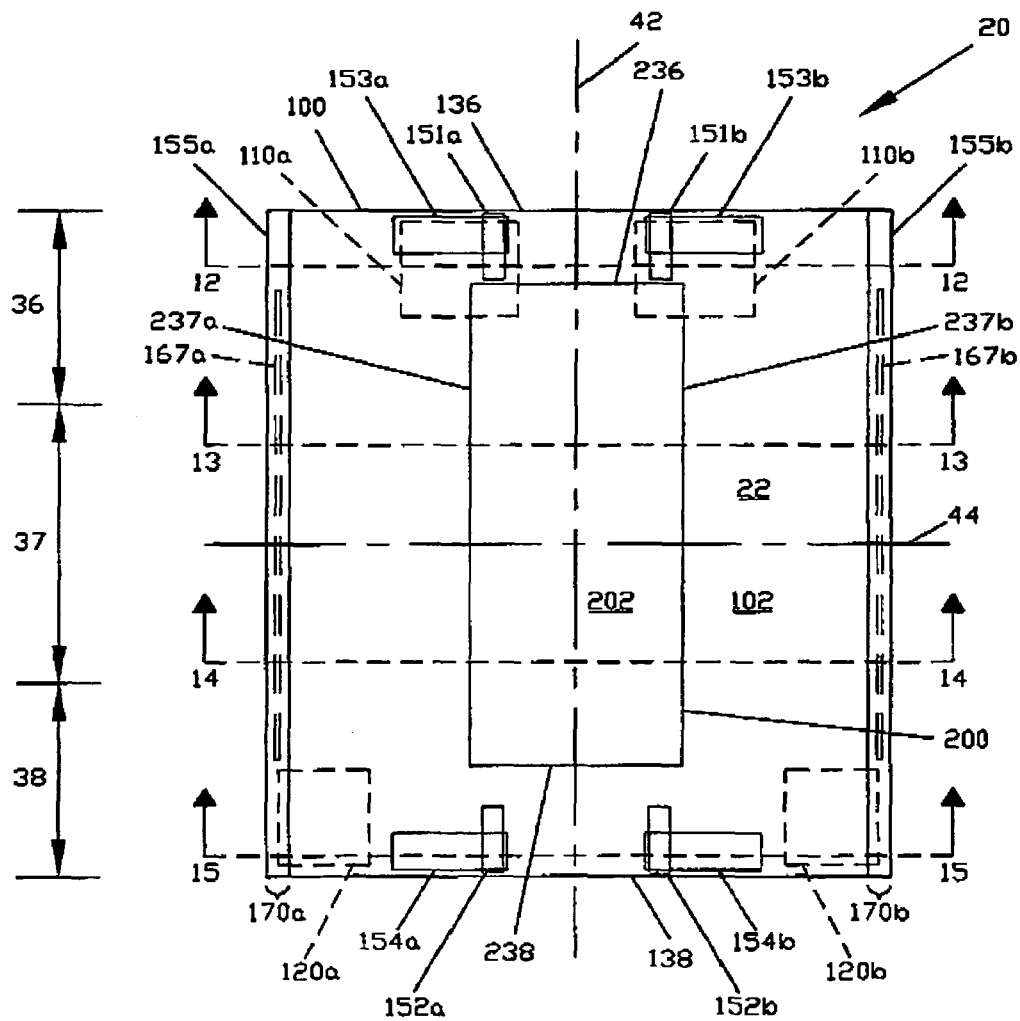
FIG. 10 is a plan view of an exemplary diaper 20 shown in its flat, uncontracted state, i.e., without the contraction induced by elastic members, before the side flaps 147a and 147b are formed by folding portions of the chassis 100 laterally inward, i.e., toward the longitudinal axis 42.
Figure 11:
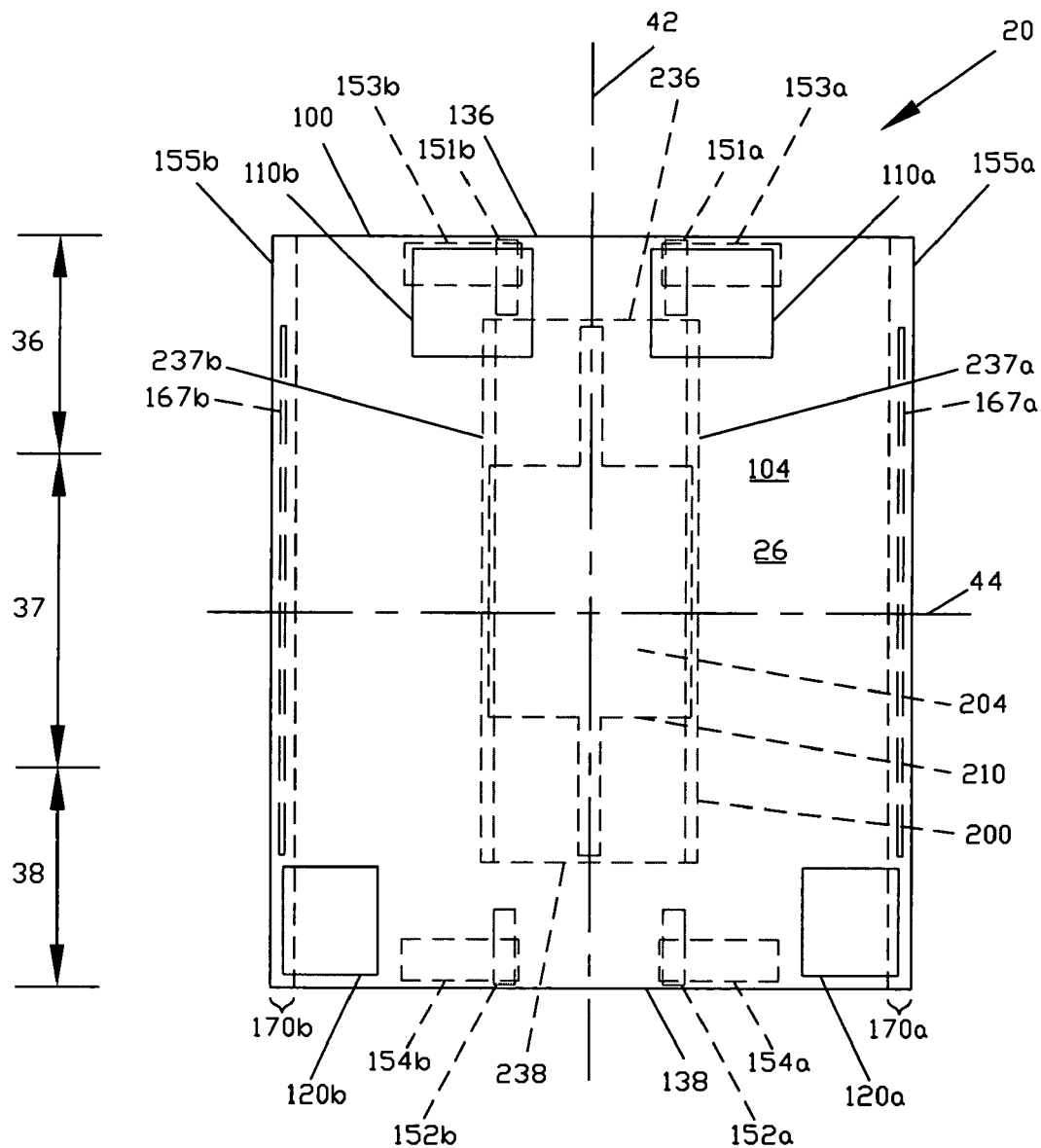
FIG. 11 is a plan view of the diaper 20 of FIG. 10 in its flat, uncontracted state, with the exterior portion of the diaper 20 that faces outwardly away from the wearer shown facing the viewer.
Figure 12:
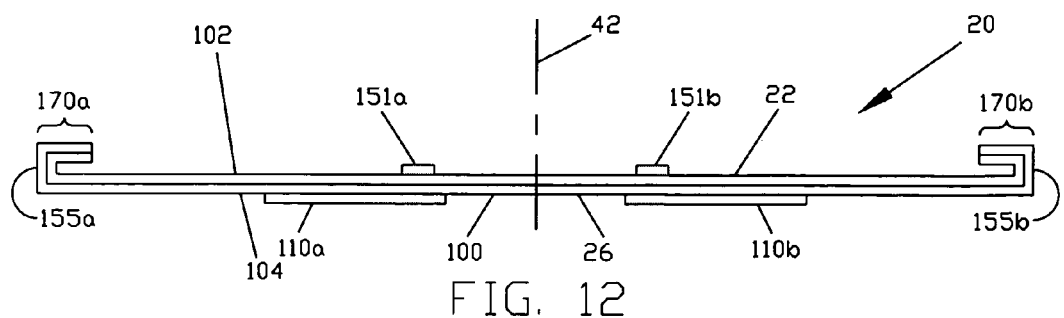
FIG. 12 is a section view of the diaper 20 of FIG. 10 taken at the section line 12-12.
Figure 13:
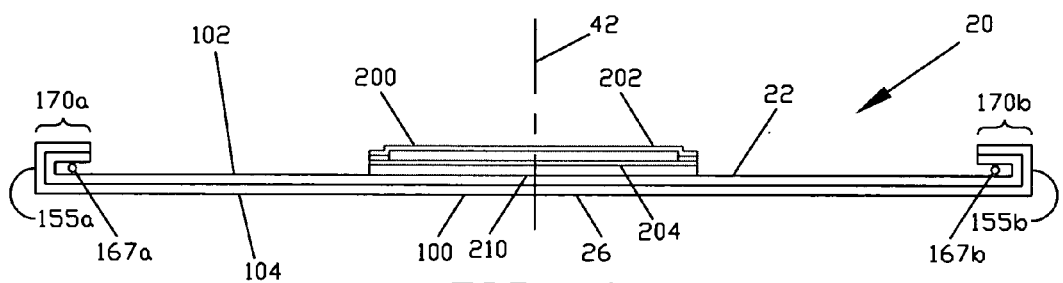
FIG. 13 is a section view of the diaper 20 of FIG. 10 taken at the section line 13-13.
Figure 14:
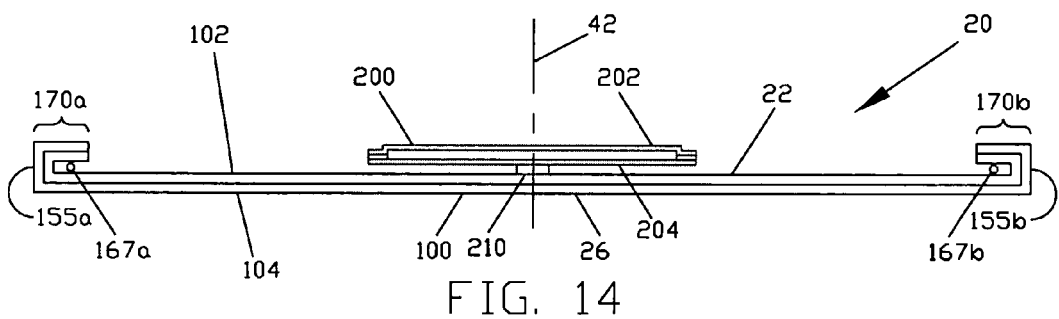
FIG. 14 is a section view of the diaper 20 of FIG. 10 taken at the section line 14-14.
Figure 15:
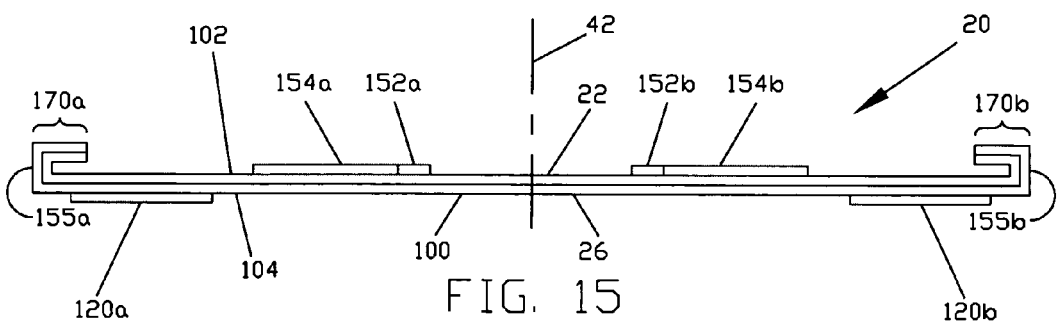
FIG. 15 is a section view of the diaper 20 of FIG. 10 taken at the section line 15-15.

As shown in FIG. 7, FIG. 8, and FIG. 9, when the diaper 20 is worn on the lower torso of a wearer, the front waist edge 136 and the back waist edge 138 encircle the waist of the wearer, while at the same time the chassis side edges 137*a* and 137*b* encircle the legs of the wearer. At the same time, the crotch region 37 is generally positioned between the legs of the wearer and the absorbent assembly 200 extends from the front waist region 36 through the crotch region 37 to the back waist region 38.

Description of the Chassis

In FIG. 10, FIG. 11, FIG. 12, FIG. 13, FIG. 14, and FIG. 15, the exemplary chassis 100 is shown laid out flat before the side flaps 147*a* and 147*b* are formed by folding portions of the chassis 100 laterally inward, i.e., toward the longitudinal axis 42, to form both the respective side flaps 147*a* and 147*b* and the side edges 137*a* and 137*b* of the chassis 100 as shown in FIG. 1, FIG. 2, FIG. 3, FIG. 4, FIG. 5, and FIG. 6. In this condition of being laid out flat, the chassis 100 has a longitudinally extending left outer side edge 155*a* and a laterally opposing and longitudinally extending right outer side edge 155*b*. Both of these chassis outer side edges extend longitudinally between the front waist edge 136 and the back waist edge 138. As is described in more detail below, when the side flaps 147*a* and 147*b* are formed by folding portions of the chassis 100 laterally inward, the outer side edges 155*a* and 155*b* of the chassis form the respective proximal edges 157*a* and 157*b* of the side flaps.

The chassis 100 includes a water-impermeable backsheet 26. The backsheet 26 forms an exterior surface that is intended to be placed toward any clothing that is worn over the diaper 20. Many suitable materials for use as the backsheet 26 are well-known, including films of polyethylene and other polyolefins. Multi-layer backsheets, such as laminates of a film and a nonwoven, are also well-known and may be suitable for use as the backsheet 26. Such a laminate backsheet may be oriented with the nonwoven disposed exteriorly to provide the feel and appearance of a more cloth-like outermost layer than would be provided by using the film as the outermost layer.

The chassis 100 may, but need not, additionally include an inner liner 22 attached to the backsheet 26. The inner liner 22 may form a portion of the interior surface 102 of the chassis 100 that is intended to be placed against the body of the wearer. The inner liner 22 preferably is formed of a soft material that will not irritate the skin of the wearer. Such an inner liner 22 may serve to isolate the skin of the wearer from a portion of the backsheet 26 as may be desirable, for example, when the diaper 20 is worn under conditions in which contact between the skin and a backsheet film could be uncomfortable. Many suitable materials for the inner liner 22 are well-known in the art, including rayon and synthetic nonwovens such as spunbonded or carded polypropylene or polyester. The inner liner 22 may extend to the same width and the same length as the backsheet 26. For example, in the exemplary chassis 100 shown in FIG. 10 and FIG. 11, the edges of the inner liner 22 are not separately identified because the inner liner 22 has the same extent as the backsheet 26.

Alternatively, one or more of the edges of the inner liner 22 may lie inward of the edges of the backsheet 26. For example, with reference to the exemplary diaper 20 shown in FIG. 1, only the portions of the inner liner 22 lying in the gaps between the front edge 236 of the absorbent assembly 200 and the front waist edge 136 of the chassis 100 and between the back edge 238 of the absorbent assembly 200 and the back waist edge 138 of the chassis 100 are exposed, while the remainder of the inner liner 22 is covered by the absorbent assembly 200 and the side flaps 147*a* and 147*b*. Therefore, a laterally extending strip of the inner liner 22 disposed in the gap in the front waist region 36 and a similar laterally extending strip of the inner liner 22 disposed in the gap in the back waist region 38 may suffice to isolate the skin of the wearer from the backsheet 26 in these two gaps.

As shown in FIG. 1, FIG. 2, FIG. 3, FIG. 4, FIG. 5, and FIG. 6, the exemplary chassis 100 has longitudinally extending and laterally opposing side flaps 147*a* and 147*b* that are disposed on the interior portion of the diaper 20 that faces inwardly toward the wearer and contacts the wearer. The side flaps 147*a* and 147*b* may be formed by folding portions of the chassis 100 laterally inward, i.e., toward the longitudinal axis 42, to form both the respective side flaps 147*a* and 147*b* and the side edges 137*a* and 137*b* of the chassis 100. Alternatively, the side flaps 147*a* and 147*b* may be formed by attaching an additional layer or layers to the chassis 100 at or adjacent to each of the respective side edges 137*a* and 137*b* of the chassis 100. In embodiments in which the side flaps are formed by attaching an additional layer or layers to the chassis, each of the additional layer or layers may be attached at or adjacent to its laterally distal edge.

Portions of a film backsheet 26 that are folded laterally inward to form the side flaps may contact the skin of a wearer during the use of the diaper 20. However, the alternating ridges and valleys in such a film backsheet that has been deformed in order to make it extensible may provide channels through which air can pass to alleviate any concern regarding such contact of the film backsheet with the skin.

In embodiments in which portions of the chassis 100 are folded laterally inward to form the side flaps 147a and 147b, the chassis 100 may simply be folded loosely or may be creased along a portion of each of its side edges 137a and 137b. For example, it may be desirable to form creases along portions of the side edges 137a and 137b in the crotch region 37 in order to impart a more finished appearance to the diaper 20. Alternatively or in addition to creasing, a portion of each of the folded side flaps 147a and 147b adjacent to the side edges 137a and 137b may be attached to the interior surface 102 of the chassis 100 to achieve a similar result.

The left side flap 147a has a proximal edge 157a and the right side flap 147b has a proximal edge 157b. In the exemplary diaper 20 shown in FIG. 1, the left side flap 147a and the right side flap 147b overlap the absorbent assembly 200, i.e., the proximal edge 157a and the proximal edge 157b lie laterally inward of the respective left side edge 237a and right side edge 237b of the absorbent assembly 200. Such an overlapped configuration may be desirable in order to impart a more finished appearance to the diaper 20 than that imparted by a non-overlapped configuration. Alternatively, the left side flap 147a and the right side flap 147b may not overlap the absorbent assembly 200, i.e., the proximal edge 157a and the proximal edge 157b may lie laterally outward of the respective left side edge 237a and right side edge 237b of the absorbent assembly 200.

In the exemplary chassis 100 shown in FIG. 1, the left side flap 147a and the right side flap 147b extend the full length of the chassis 100 between the front waist edge 136 and the back waist edge 138. Such a full length configuration may be desirable in order to minimize the amount of waste material and the difficulty associated with the manufacture of the diaper 20, especially when the method used to manufacture the diaper 20 requires the introduction of the material or materials for the chassis 100 in the form of a continuous web or multiple continuous webs. Alternatively, the side flaps may be shorter and extend less than the full distance between the front waist edge 136 and the back waist edge 138. Such a shorter configuration may be desirable in order to minimize the total amount of material used in the manufacture of the diaper 20.

Each of the side flaps 147a and 147b is attached to the interior surface 102 of the chassis 100 in attachment zones located in the front waist region 36 and in the back waist region 38. For example, in the chassis 100 shown in FIG. 1, the side flaps 147a and 147b are attached to the interior surface 102 of the chassis 100 in the adhesive attachment zones that are shown there and that are more clearly visible in FIG. 10, where the chassis 100 is shown laid out flat before the side flaps 147a and 147b are formed. In particular, the left side flap 147a is attached to the interior surface 102 of the chassis 100 in a longitudinally oriented adhesive attachment zone 151a adjacent to its proximal edge 157a near the front waist edge 136 and in a longitudinally opposing longitudinally oriented adhesive attachment zone 152a adjacent to its proximal edge 157a near the back waist edge 138. Similarly, the right side flap 147b is attached to the interior surface 102 of the chassis 100 in a longitudinally oriented adhesive attachment zone 151b adjacent to its proximal edge 157b near the front waist edge 136 and in a longitudinally opposing longitudinally oriented adhesive attachment zone 152b adjacent to its proximal edge 157b near the back waist edge 138. The adhesive attachment zones may have equal areas or may be unequal in area. For example, the front longitudinally oriented adhesive attachment zones 151a and 151b may be of one size and the back longitudinally oriented adhesive attachment zones 152a and 152b may be of another size.

In the exemplary chassis 100 shown in FIG. 1, the left side flap 147a is also attached to the interior surface 102 of the chassis 100 in a laterally oriented adhesive attachment zone 153a adjacent to the front waist edge 136 and in a longitudinally opposing laterally oriented adhesive attachment zone 154a adjacent to the back waist edge 138. Similarly, the right side flap 147b is attached to the interior surface 102 of the chassis 100 in a laterally oriented adhesive attachment zone 153b adjacent to the front waist edge 136 and in a longitudinally opposing laterally oriented adhesive attachment zone 154b adjacent to the back waist edge 138. The adhesive attachment zones may have equal areas or may be unequal in area. For example, the front laterally oriented adhesive attachment zones 153a and 153b may be of one size and the back laterally oriented adhesive attachment zones 154a and 154b may be of another size.

Alternatively, each attachment zone may extend laterally across the full width of the respective side flap. For example, a laterally oriented adhesive attachment zone may extend laterally from the chassis left side edge 137a to the left side flap edge 157a and thereby attach the entire width of the left side flap 147a adjacent to the front waist edge 136 to the interior surface 102 of the chassis 100. In embodiments in which the front edge 236 or the back edge 238 of the absorbent assembly 200 coincides with the respective front waist edge 136 or back waist edge 138 of the chassis 100 and the side flaps 147a and 147b overlap the absorbent assembly 200, the side flaps 147a and 147b may be attached to the absorbent assembly 200 instead of, or in addition to, being attached to the interior surface 102 of the chassis 100.

Between the attachment zones, the proximal edges 157a and 157b of the side flaps 147a and 147b remain free, i.e., are not attached to the interior surface 102 of the chassis 100 or to the absorbent assembly 200. Also between the attachment zones, each side flap preferably includes a longitudinally extensible flap elastic member that is attached adjacent to the proximal edge of the side flap by any of many well-known means. Each such flap elastic member may be attached over its entire length or over only a portion of its length. For example, such a flap elastic member may be attached only at or near its longitudinally opposing ends and may be unattached at the middle of its length. Such a flap elastic member may be disposed in the crotch region 37 and may extend into one or both of the front waist region 36 and the back waist region 38. For example, in the exemplary chassis 100 shown in FIG. 1, an elastic strand 167a is attached adjacent to the proximal edge 157a of the left side flap 147a and extends into both the front waist region 36 and the back waist region 38. Similarly, an elastic strand 167b is attached adjacent to the proximal edge 157b of the right side flap 147b and extends into both the front waist region 36 and the back waist region 38.

Each flap elastic member may be enclosed inside a folded hem. For example, in the exemplary chassis 100 shown in FIG. 4 and FIG. 5, the elastic strand 167a is enclosed inside a hem 170a formed adjacent to the proximal edge 157a of the left side flap 147a and the elastic strand 167b is enclosed inside a hem 170b formed adjacent to the proximal edge 157b of the right side flap 147b. Alternatively, the flap elastic member may be sandwiched between two layers of the chassis, e.g., between the layers of a laminate backsheet or between a backsheet and an inner liner. As another alternative, the flap elastic member may be attached on a surface of the chassis 100 and remain exposed.

Figure 16:
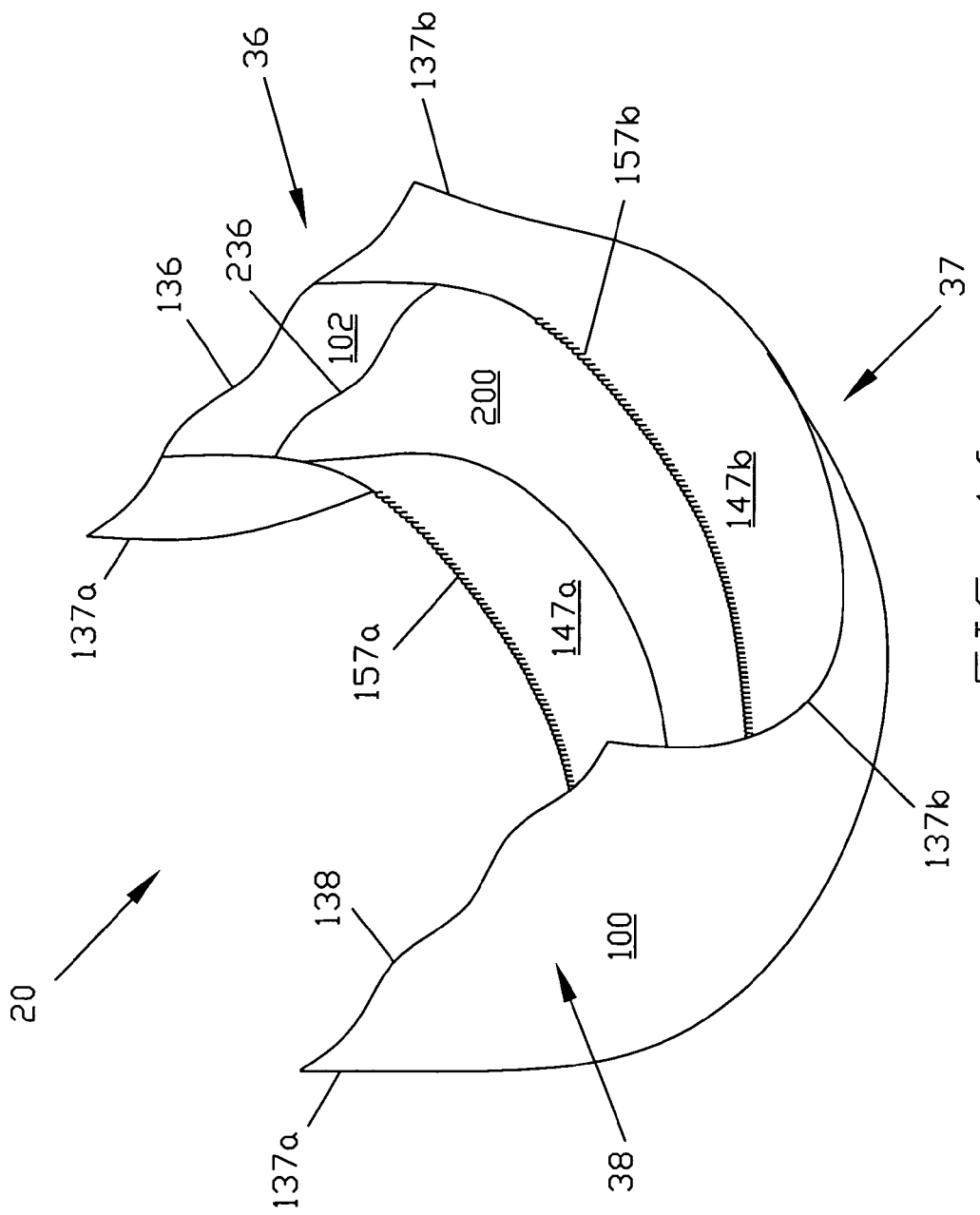
FIG. 16 is a perspective view of an exemplary diaper 20, which is shown in its relaxed, contracted state, i.e., with the contraction induced by elastic members.

When stretched, the flap elastic member adjacent to each side flap edge allows the side flap edge to extend to the flat uncontracted length of the chassis, e.g., the length of the chassis 100, as shown in FIG. 1. When allowed to relax, the flap elastic member contracts to gather the portion of the side flap edge along which the flap elastic member is attached and thereby make the relaxed length of the side flap edge less than the flat uncontracted length of the chassis. For example, when the exemplary diaper 20 is in a relaxed condition as shown in FIG. 16, the elastic strand 167a contracts to gather the proximal edge 157a of the left side flap 147a and the elastic strand 167b contracts to gather the proximal edge 157b of the right side flap 147b. The contractive forces of the elastic strands 167a and 167b are transmitted at the respective front attachment zones 151a and 151b to the interior surface 102 of the chassis 100 at the front waist region 36. Similarly, the contractive forces of the elastic strands 167a and 167b are transmitted at the respective back attachment zones 152a and 152b to the interior surface 102 of the chassis 100 at the back waist region 38. These contractive forces pull the front waist region 36 and the back waist region 38 toward each other and thereby bend the diaper 20 into a "U" shape in which the interior of the "U" shape is formed by the portions of the diaper 20 that are intended to be placed toward the body of the wearer. Because the proximal edge 157a remains free between the attachment zones 151a and 152a, the contractive force of the elastic strand 167a lifts the proximal edge 157a away from the interior surface 102 of the chassis 100. Similarly, because the proximal edge 157b remains free between the attachment zones 151b and 152b, the contractive force of the elastic strand 167b lifts the proximal edge 157b away from the interior surface 102 of the chassis 100. As shown in FIG. 16, this lifting of the proximal edges 157a and 157b when the diaper 20 is in the relaxed condition lifts the side flaps 147a and 147b into position to serve as side barriers adjacent to the side edges 237a and 237b of the absorbent assembly 200.

When the diaper 20 is worn, the relaxed "U" shape generally conforms to the body of the wearer such that the front waist region 36 and the back waist region 38 can be fastened together to encircle the waist and the legs of the wearer. When the diaper 20 is worn in this manner, the elastic strands 167a and 167b tend to hold the lifted proximal edges 157a and 157b of the side flaps 147a and 147b in contact with the body of the wearer and thereby form seals to help prevent the leakage of deposited bodily waste out of the diaper 20. The lateral spacing of the lifted proximal edges 157a and 157b is selected to allow the deposit of bodily wastes from the lower torso of the wearer into the space between the lifted side flaps 147a and 147b and thereby directly onto the absorbent assembly 200. The width of each of the side flaps 147a and 147b in effect becomes its height when the free portion of its proximal edge is lifted and the side flap serves as a side barrier to leakage. This height preferably is selected to allow the lifted proximal edges 157a and 157b to fit into the leg creases of the body of the wearer at the same time as the absorbent assembly 200 is held in contact with the body.

Figure 2:
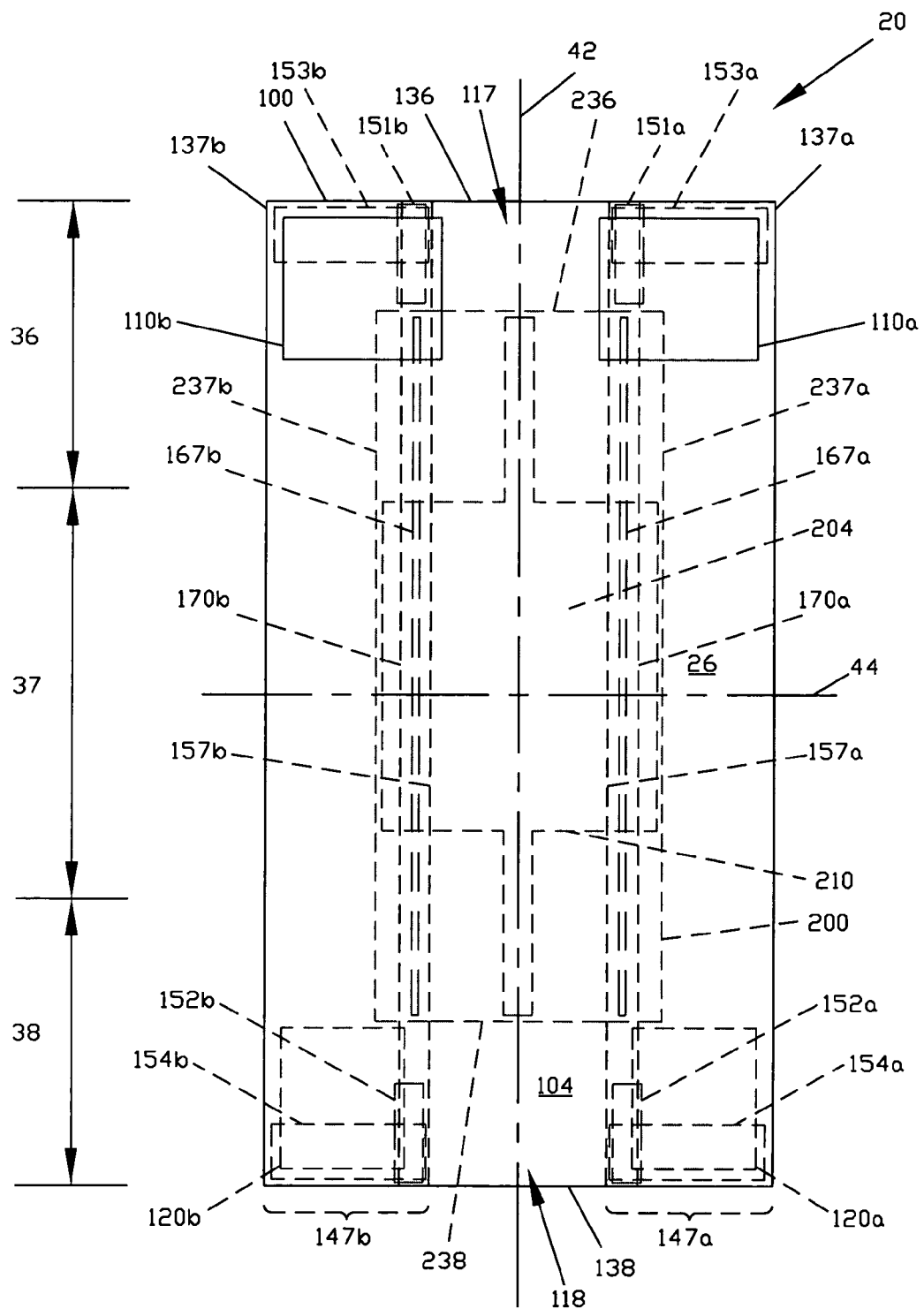
FIG. 2 is a plan view of the diaper 20 of FIG. 1 in its flat, uncontracted state, with the exterior portion of the diaper 20 that faces outwardly away from the wearer shown facing the viewer.

In the finished diaper, the chassis may have a generally rectangular shape, as in the exemplary diaper 20 shown in FIG. 1 and FIG. 2. Such a generally rectangular configuration may be desirable in order to minimize the amount of waste material and the difficulty associated with the manufacture of the diaper 20. Alternatively, the chassis may have side edges 137a and 137b that are not straight, but instead are curved and/or notched, thereby giving an overall shape in plan view of an hourglass or of an "I" to the diaper 20. Such a non-rectangular configuration may be desirable in order to impart a tailored appearance to the diaper 20 when it is worn. Such a non-rectangular configuration may also be desirable in order to impart an impression that the diaper 20 will fit comfortably between the legs of a wearer. Any one of many well-known ways may be used to form a non-rectangular configuration of the chassis. For example, laterally distal portions may be removed from the chassis to make its lateral dimension at and adjacent to the lateral axis 44 smaller than its lateral dimension at and adjacent to the front waist edge 136 and smaller than its lateral dimension at and adjacent to the back waist edge 138, i.e., to make the chassis narrower in the crotch region 37 than at the waist edges 136 and 138. Alternatively, a portion of each of the side edges 137a and 137b may be folded laterally inward in order to achieve the same result. Such folded portions of the side edges 137a and 137b may be creased or attached, or both creased and attached, in order to prevent their unfoldment.

Figure 17:
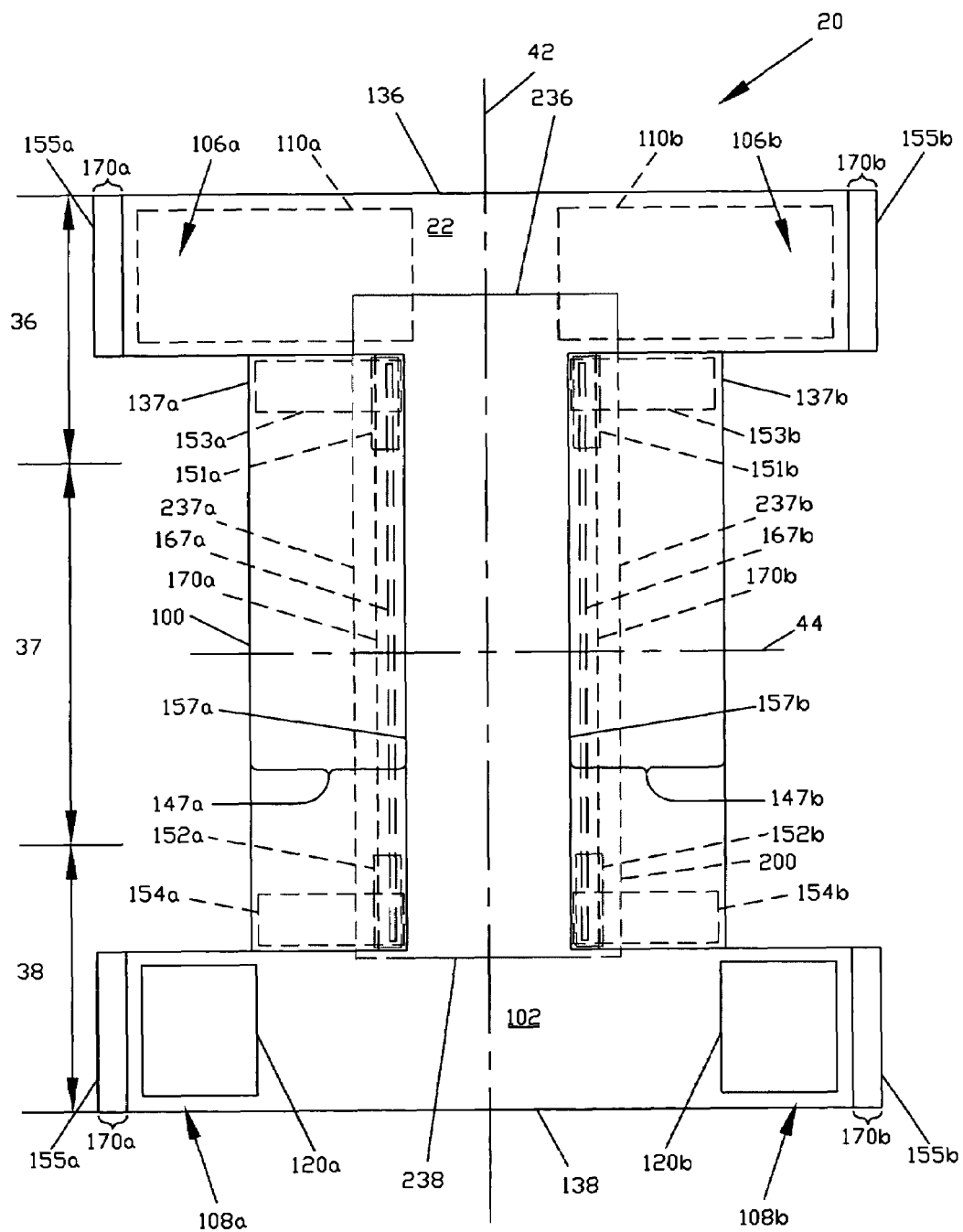
FIG. 17 is plan view of an exemplary diaper 20 shown in its flat, uncontracted state, i.e., without the contraction induced by elastic members, in which portions of the chassis are left laid out flat when other portions are folded laterally inward to form the side flaps 147a and 147b.

An exemplary form of a non-rectangular configuration of the chassis is shown in FIG. 17. As shown in this figure, portions of the chassis extending laterally between the outer side edges and the respective side edges in one or both of the waist regions may be left laid out flat, i.e., may remain unfolded, when other portions are folded laterally inward to form the side flaps. For example, as shown in FIG. 17, the portions 106a and 106b extending longitudinally from the front waist edge 136 toward the lateral axis 44 in the front waist region 36 and extending laterally between each of the outer side edges 155a and 155b and the respective side edges 137a and 137b may be left laid out flat, i.e., may remain unfolded. Similarly, the portions 108a and 108b extending longitudinally from the back waist edge 138 toward the lateral axis 44 in the back waist region 38 and extending laterally between each of the outer side edges 155a and 155b and the respective side edges 137a and 137b may be left laid out flat, i.e., may remain unfolded. Other portions extending longitudinally between the portions that remain unfolded and through the crotch region 37 may be folded laterally inward to form the side flaps 147a and 147b. The portions 106a and 106b and the portions 108a and 108b form "ears" that project laterally outward from each of the waist regions of the diaper. These ears project laterally outward beyond the inward-folded portions and impart an "I" shape to the diaper, as shown in FIG. 17. It is not necessary that portions remain unfolded at both ends as shown in FIG. 17. For example, the portions 106a and 106b in the front waist region 36 may remain unfolded and only the portions 108a and 108b in the back waist region 38 may be folded laterally inward, or vice versa, in some embodiments.

An alternative way to form an "I"-shaped non-rectangular configuration of the chassis as shown in FIG. 17 is to form the chassis in the "I" shape and attach an additional layer or layers to the interior surface of the "I"-shaped chassis at or adjacent to each of the side edges 137a and 137b of the chassis 100 to form the respective side flaps 147a and 147b. In embodiments in which the side flaps are formed by attaching an additional layer or layers to the chassis, each of the additional layer or layers may be attached at or adjacent to its laterally distal edge.

Figure 3:
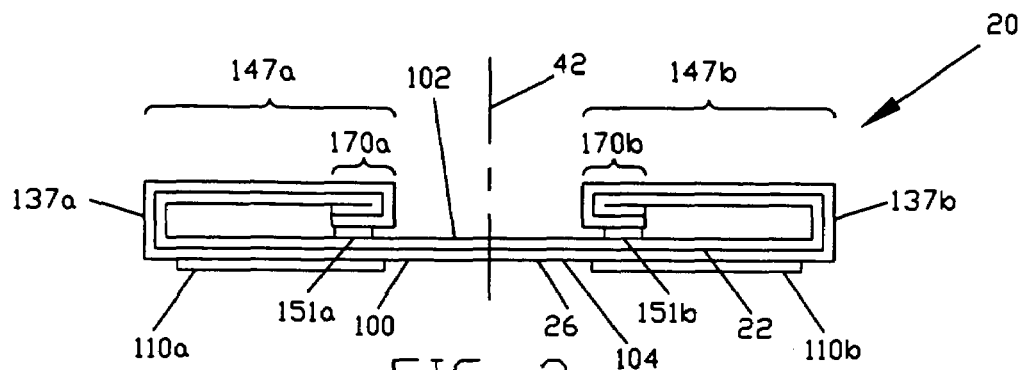
FIG. 3 is a section view of the diaper 20 of FIG. 1 taken at the section line 3-3.
Figure 4:
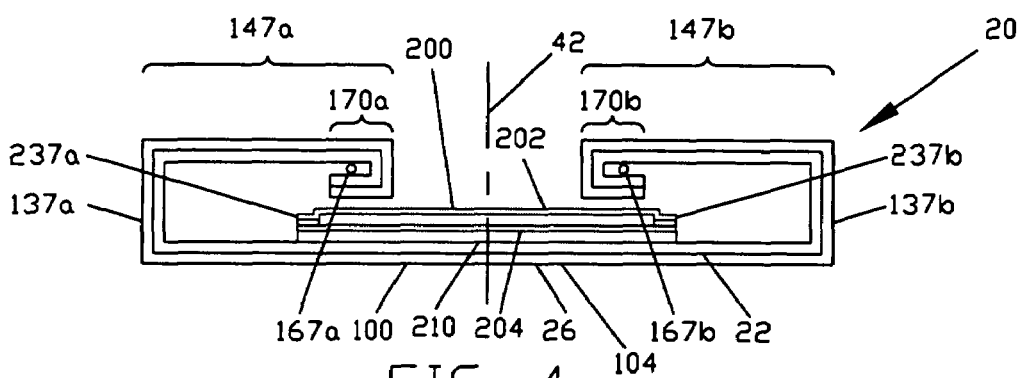
FIG. 4 is a section view of the diaper 20 of FIG. 1 taken at the section line 4-4.
Figure 5:
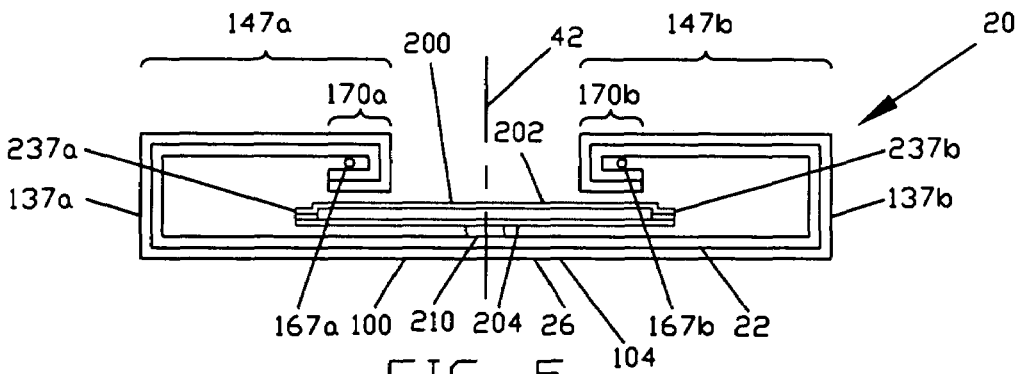
FIG. 5 is a section view of the diaper 20 of FIG. 1 taken at the section line 5-5.
Figure 6:
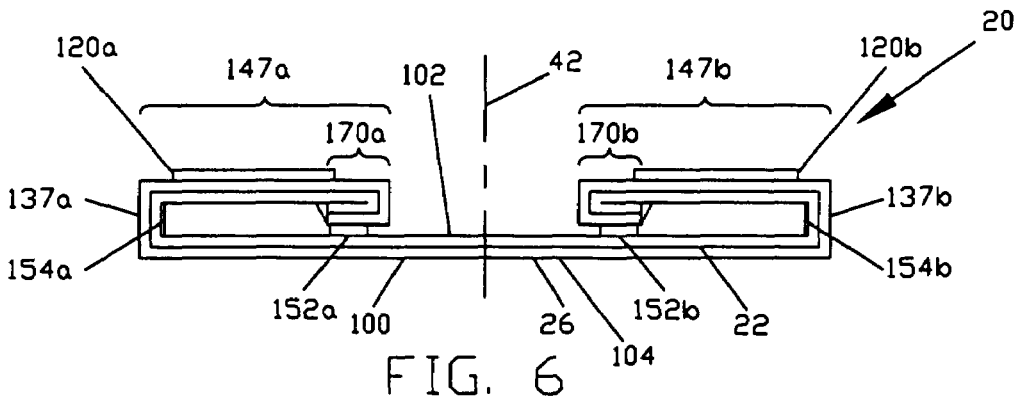
FIG. 6 is a section view of the diaper 20 of FIG. 1 taken at the section line 6-6.
Figure 18:
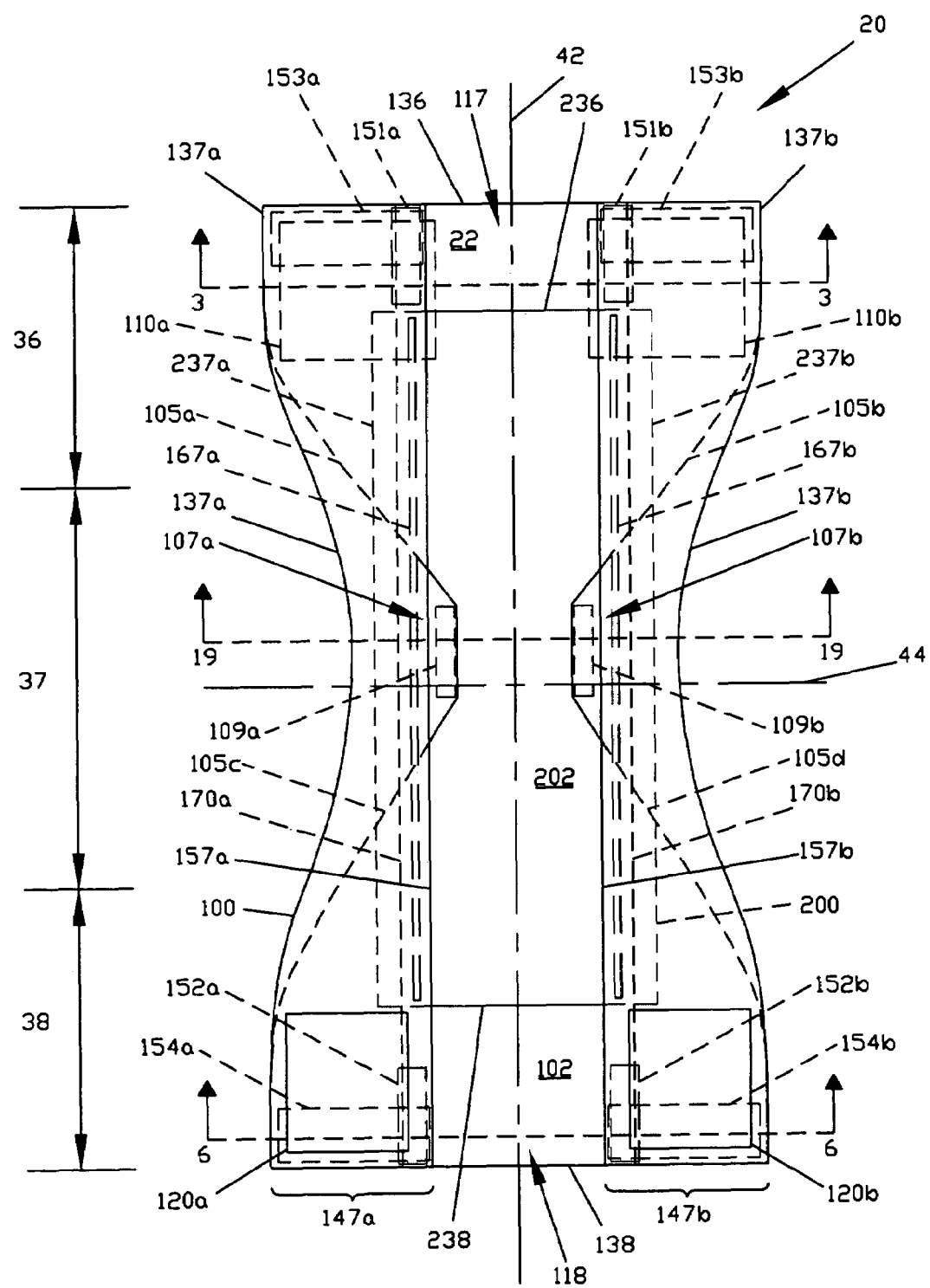
FIG. 18 is a plan view of an exemplary diaper 20 shown in its flat, uncontracted state, i.e., without the contraction induced by elastic members, in which portions of the chassis are folded over and attached to the interior surface of the absorbent assembly to impart an hourglass shape to the diaper 20.
Figure 19:
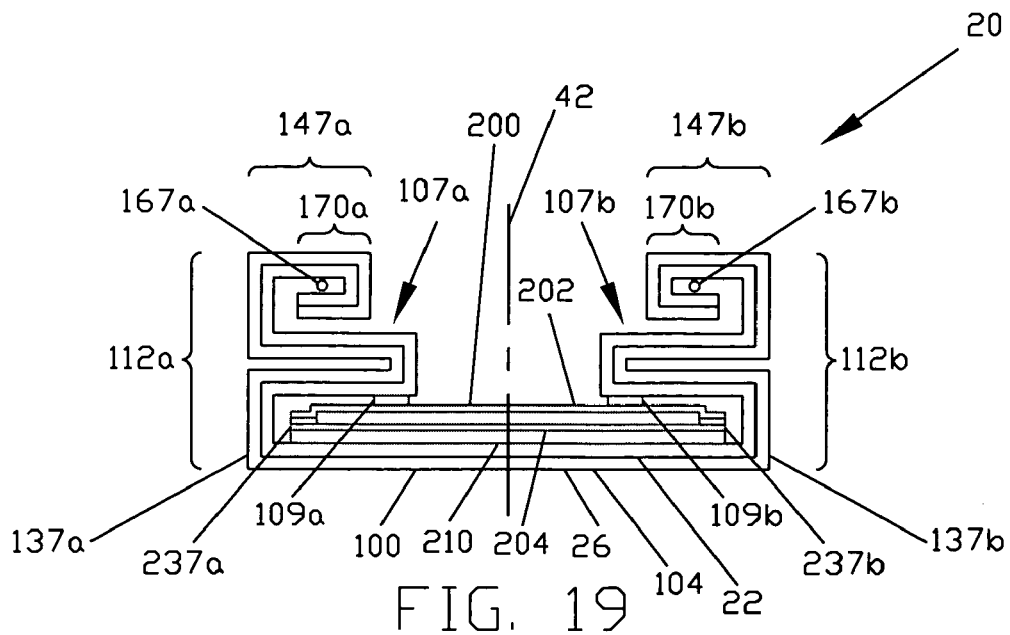
FIG. 19 is a section view of the diaper 20 of FIG. 18 taken at the section line 19-19.

Another exemplary way to form a non-rectangular configuration of the chassis is shown in FIG. 18 and FIG. 19. As shown in these figures, laterally opposing portions 107a and 107b of the chassis between each of the side edges 137a and 137b and the respective proximal edges 157a and 157b of the side flaps 147a and 147b may be folded laterally inward in the crotch region 37 along respective diagonal fold lines 105a, 105b, 105c, and 105d such that each of the folded portions 107a and 107b of the chassis overlaps the absorbent assembly 200 in the crotch region 37. The interior surface 102 of each of the folded portions 107a and 107b may be attached to the interior surface 202 of the absorbent assembly in the crotch region 37 at attachment zones 109a and 109b. This folding and attachment forms "W" shaped folds 112a and 112b in the chassis in the crotch region 37 as shown in FIG. 19, while retaining the configuration of the waist regions 36 and 38 as shown in FIG. 3 and FIG. 6. The overall effect on the shape of the chassis is to form an hourglass-shaped configuration as shown in FIG. 18. The attachment zones 109a and 109b may be disposed symmetrically with respect to either or both of the longitudinal axis 42 and the lateral axis 44. Alternatively, the attachment zones 109a and 109b may be disposed asymmetrically with respect to either or both of the longitudinal axis 42 and the lateral axis 44. For example, the attachment zones 109a and 109b shown in FIG. 18 are disposed symmetrically with respect to the longitudinal axis 42 and asymmetrically with respect to the lateral axis 44. In particular, the attachment zones 109a and 109b shown in FIG. 1 are disposed asymmetrically toward the front waist region 36.

Alternatively, the laterally opposing portions 107a and 107b of the chassis may be folded laterally inward in one or both of the waist regions in addition to being folded laterally inward in the crotch region. For example, in order to simplify the manufacture of the diaper, the laterally opposing portions 107a and 107b of the chassis may be folded laterally inward over their entire longitudinal lengths. The interior surface 102 of each of the folded portions 107a and 107b may be attached to the interior surface 202 of the absorbent assembly in the crotch region 37 at attachment zones 109a and 109b. This folding and attachment forms "W" shaped folds 112a and 112b in the chassis as shown in FIG. 19 over the entire longitudinal lengths of the laterally opposing portions 107a and 107b of the chassis. An hourglass shape may subsequently be imparted to the chassis when the laterally opposing portions are laterally extended by unfolding at their longitudinally distal ends to prepare the disposable diaper for use in the configuration shown in FIG. 18.

A portion or the whole of the chassis 100 may be made extensible to a degree greater than the inherent extensibility of the material or materials from which the chassis is made, e.g, the backsheet 26, the inner liner 22, or both. The additional extensibility may be desirable in order to allow the chassis 100 to conform to the body of a wearer during movement by the wearer. The additional extensibility may also be desirable, for example, in order to allow the user of a diaper 20 including a chassis 100 having a particular size before extension to extend the front waist region 36, the back waist region 38, or both waist regions of the chassis 100 to encircle the waist of an individual wearer whose waist circumference falls within a predefined range, i.e., to tailor the diaper to the individual wearer. Such extension of the waist region or regions may give the diaper a generally hourglass shape, so long as the crotch region 37 is extended to a relatively lesser degree than the waist region or regions, and may impart a tailored appearance to the diaper 20 when it is worn. In addition, the additional extensibility may be desirable in order to minimize the cost of the diaper. For example, an amount of material that would otherwise be sufficient only to make a relatively smaller diaper lacking this extensibility can be used to make a diaper capable of being extended to fit a wearer larger than the smaller diaper would fit. In other words, a lesser amount of material is needed in order to make a diaper capable of being properly fit onto a given size of a wearer when the material is made extensible as described.

Additional extensibility in the chassis 100 in the lateral direction is relatively more useful than additional extensibility in the longitudinal direction. The abdomen of the wearer is likely to expand when the wearer changes posture from standing to sitting and the corresponding abdominal expansion increases the circumference that is encircled by the waist edges of the chassis 100, necessitating the lateral extension of the waist region or regions.

Figure 20:
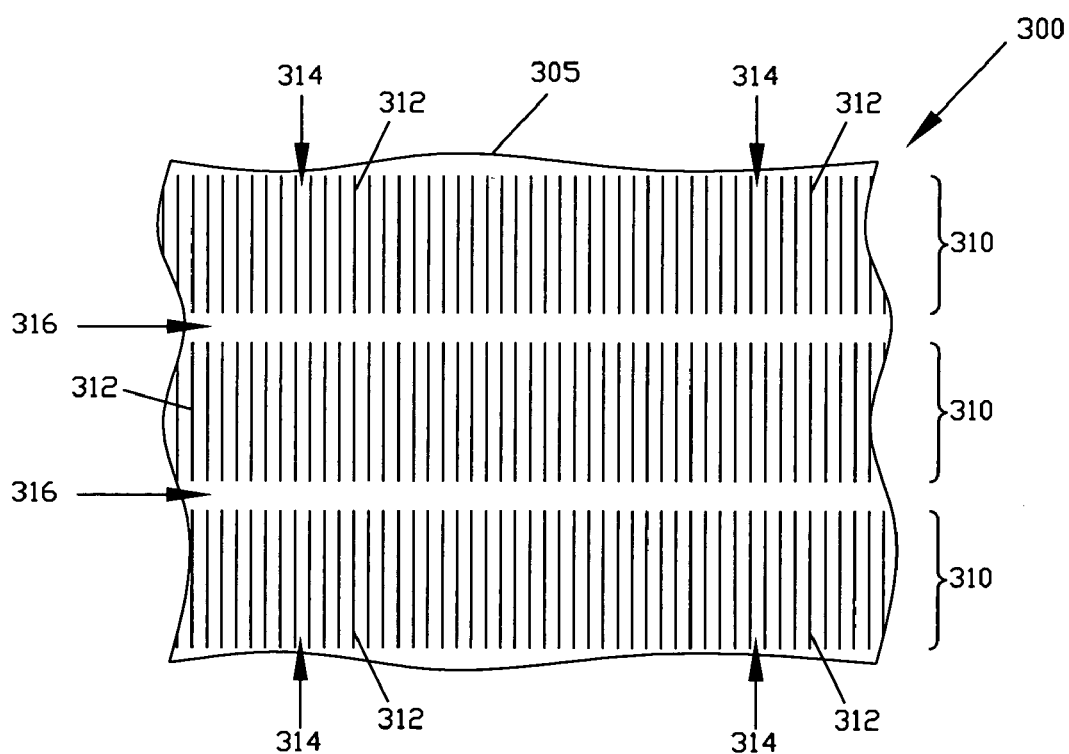
FIG. 20 is a plan view of an exemplary fragment of a formed web material.

Additional lateral extensibility in the chassis 100 may be provided in a variety of ways. For example, a material or materials from which the chassis 100 is made may be pleated by any of many known methods. Alternatively, all or a portion of the chassis may be made of a formed web material or a formed laminate of web materials like those described in U.S. Pat. No. 5,518,801 issued on 21 May 1996 in the name of Chappell et al. An exemplary fragment 300 of such a formed web material 305 is shown in FIG. 20. This formed web material 305 includes distinct laterally extending regions 310 in which the original material has been altered by embossing or another method of deformation to create a pattern of generally longitudinally oriented alternating ridges 312 and valleys 314. The formed web material 305 also includes laterally extending unaltered regions 316 located between the laterally extending altered regions 310.

Such a formed web material 305 can be laterally extended beyond its original dimension with the application of relatively less force than that required to extend the same material to the same extent when undeformed. In particular, the effects of an application of opposing divergent forces directed generally perpendicular to the ridges 312 and valleys 314 include an extension of such a formed web material along an axis between the opposing forces and the generation of a resistive contractive force, primarily in the unaltered regions 316. This resistive force is relatively smaller than the resistive force that is generated by the same material in its unaltered form when extended to the same extent, at least up to an extension at which the ridges and valleys in the altered regions flatten and begin to contribute to the resistive force. Thus, such formed web materials exhibit an extensible behavior resembling that of traditional elastic materials in the range of extensibility that is useful for the type of lateral extension desired for use in absorbent articles. However, such formed web materials may be made of relatively less expensive materials that are not inherently elastic and, thus, their use may provide an advantage in terms of the cost of manufacturing the absorbent articles.

The range of extensibility of a web material or a laminate that is formed as described in the Chappell et al. '801 patent can be controlled by the degree of deformation of the altered regions and can be varied from near zero to a maximum that is dependent upon the original material. For example, the materials used in the chassis 100 of the exemplary diaper 20 may typically be formed to provide any range of extensibility from near zero to a maximum of more than 100 percent of the original dimension. In some embodiments of the present invention, a portion of the chassis 100 may have a maximum extensibility of approximately 20 percent of its original dimension. However, any particular value for the maximum extensibility in the range from approximately one percent to approximately 100 percent may be selected to suit a particular choice of the original size of the diaper 20 and the range of sizes of the intended wearers. In particular, a diaper having a specific unextended waist opening circumference may be suitable for use on wearers having waist circumferences ranging from equal to this unextended waist opening circumference up to the maximum extensibility.

The front laterally central portion 117 and the back laterally central portion 118 of the chassis 100 between the attachment zones 151, 152, 153, and 154 where the side flaps 147a and 147b are attached to the interior surface 102 of the chassis adjacent to the respective waist edges 137 and 138 may have a different range of extensibility from the portions of the chassis in the attachment zones. Additionally or alternatively, the laterally central portions 117 and 118 may be extensible to a greater or lesser degree when subjected to a given level of opposing tensile forces, i.e., may be more easily or less easily extensible, than the portions of the chassis in the attachment zones. For example, if the chassis is made uniformly extensible across its entire width prior to the formation of the side flaps, the double layering in the areas of the attachment zones after the formation of the side flaps may have an effect of decreasing the degree of lateral extensibility of those areas under a given level of opposing tensile forces, such as by the side flaps acting as parallel "springs" that must be extended in order to extend the underlying attached portion of the chassis. As another example, the altered regions in the laterally central portions of the chassis may be deformed to a greater or a lesser degree than the altered regions in the attachment zones to render the laterally central portions more easily or less easily extensible than the respective portions in the attachment zones.

Such differential range of extensibility and/or differential relationship of tensile force to extensibility may be desirable. For example, when the waist regions are laterally extended by a user when applying a diaper to the body of a wearer, each waist region is typically subjected to a generally uniform level of opposing tensile forces across its entire width, so long as the user grasps the diaper at or adjacent to the laterally opposing side edges. If the laterally central portion of the chassis is less easily extensible than the portions in the attachment zones, the lateral spacing between the proximal edges 157a and 157b of the side flaps will increase less under a given level of applied tensile forces than if the laterally central portion were equally easily extensible or more easily extensible than the portions in the attachment zones. This effect of minimizing the change in the lateral spacing between the side flaps may help to ensure that the diaper fits as intended on the body of the wearer by, for example, making it more likely that the proximal edges 157a and 157b of the side flaps will fit into the leg creases of the body while the diaper is being worn.

Any of a variety of materials may be formed as described in the Chappell et al. '801 patent. For example, a film, a nonwoven, or a laminate of either or both of these materials may be formed to provide the desired extensibility. It is also possible to modify such a material in more than one way while forming it to provide extensibility. For example, a film that is originally formed to resist the permeation of vapor through its thickness and to contain fine particles of a granular filler material such as calcium carbonate may be treated as described in the Chappell et al. '801 patent to simultaneously provide extensibility and create small holes that allow water vapor to pass through its thickness. Thus, the film can simultaneously be rendered extensible and breathable.

The front waist region 36 and the back waist region 38 can be fastened together to encircle the waist and the legs of the wearer in many well-known ways. For example, separate fastening devices such as safety pins, separate tapes, a separate tie strap or straps, and/or a separate belt can be used for this purpose. Alternatively or in addition, fastening elements can be incorporated into the chassis 100 to enable a user to apply the diaper 20 to the body of the wearer without, or in conjunction with, any separate fastening devices. Many suitable types of such incorporated fastening elements are well-known, including, for example, tapes, adhesives, adhesive tape tabs, ties, buttons, hooks, loops, snap fasteners, other forms of mechanical fasteners, cohesive patches, etc. These incorporated fastening elements may project laterally outward, i.e., away from the longitudinal axis 42 beyond one or both of the side edges 137a and 137b and/or may project longitudinally outward, i.e., away from the lateral axis 44 beyond one or both of the waist edges 136 and 138 or they may lie entirely inside the edges of the diaper 20. When a laminate backsheet is used and is oriented with the nonwoven disposed exteriorly, some forms of mechanical fasteners that typically require specific mating fastener elements, such as hooks that mate with loops, may be configured to engage with the nonwoven and thereby make the inclusion of the specific mating fastener element unnecessary.

Figure 21:
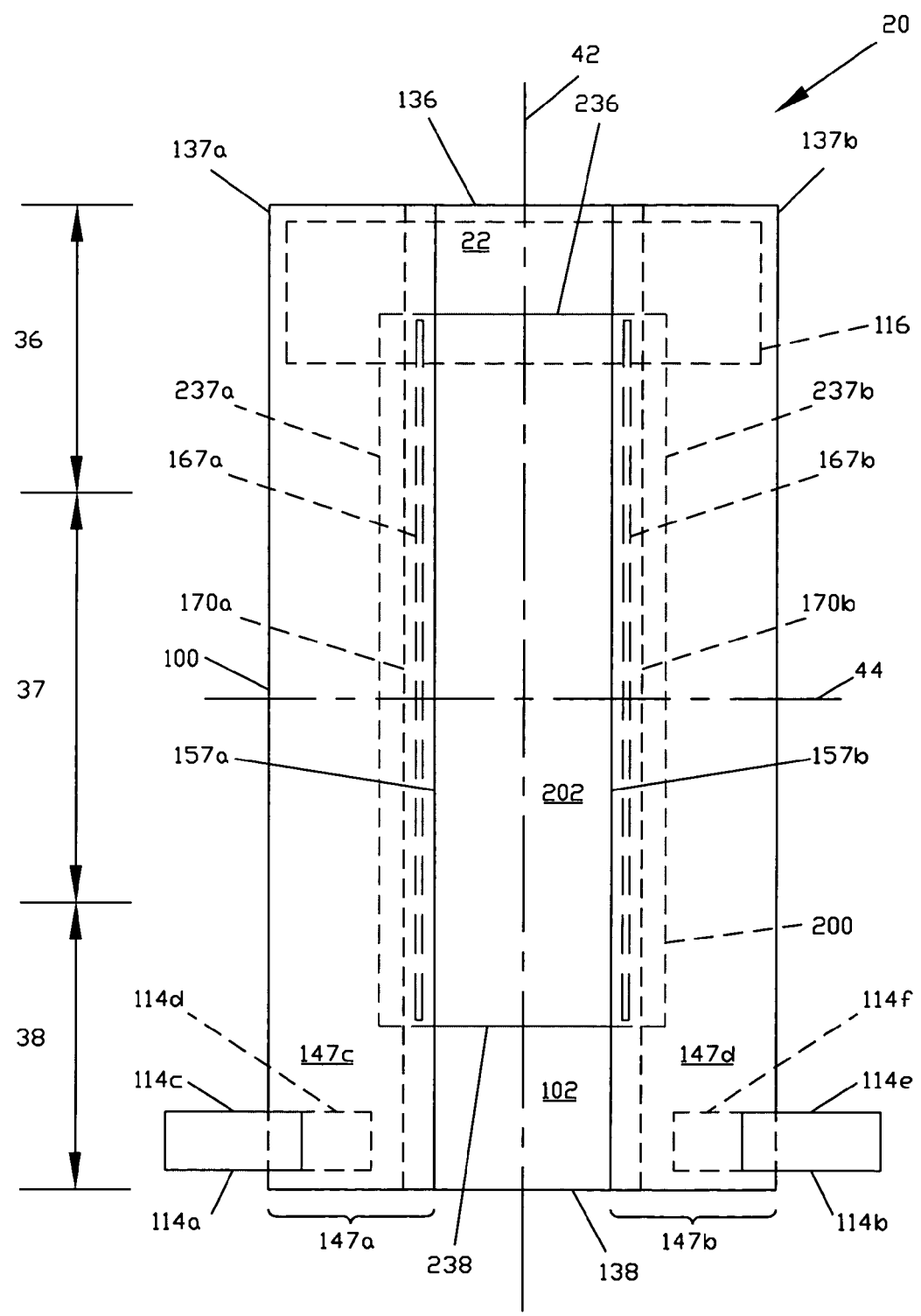
FIG. 21 is a simplified plan view of an exemplary disposable absorbent article in the form of a diaper 20, which is shown in its flat, uncontracted state, i.e., without the contraction induced by elastic members, having adhesive tape tabs 114a and 114b and a fastening surface 116 attached to the chassis.
Figure 22:
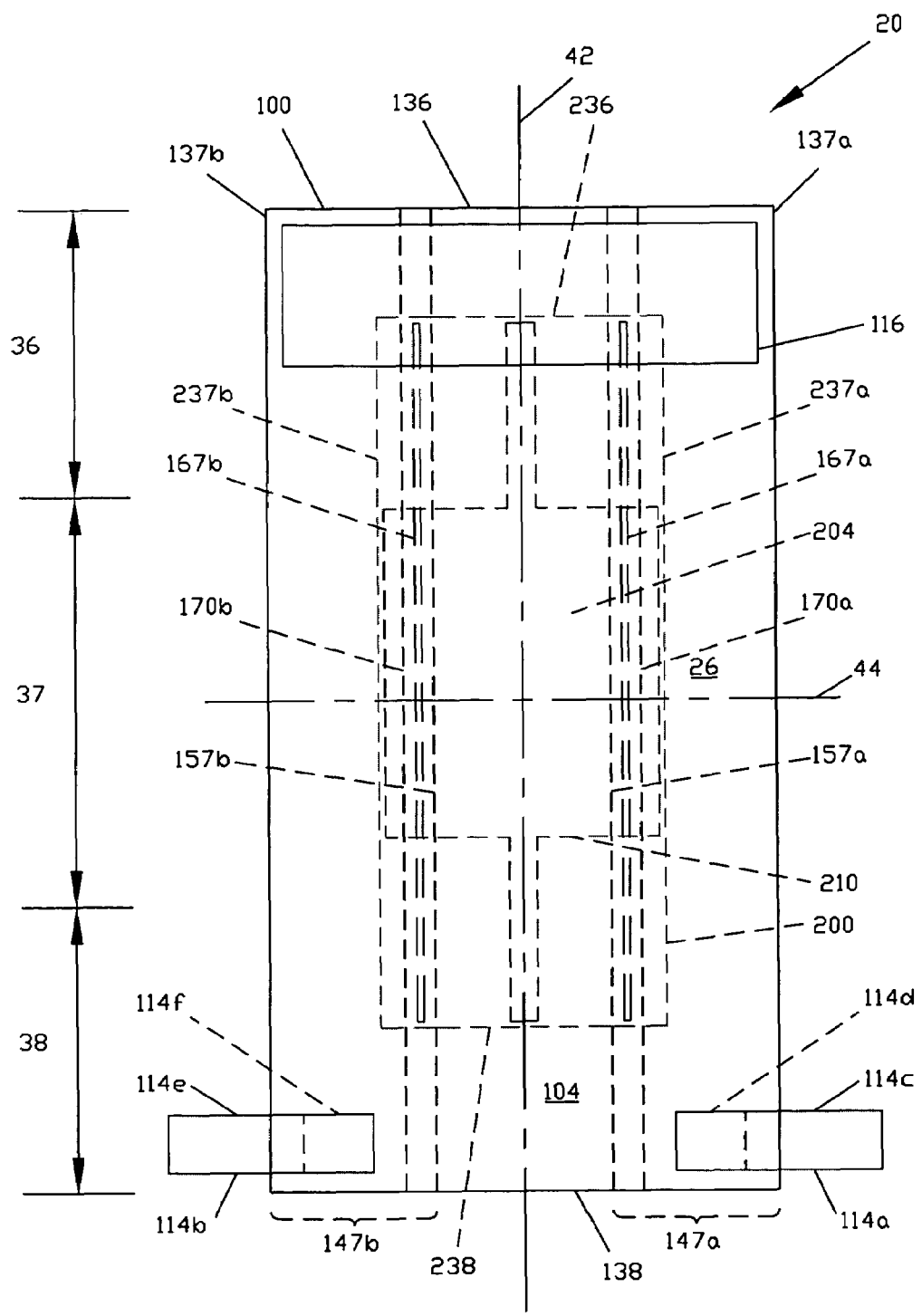
FIG. 22 is a simplified plan view of the diaper 20 of FIG. 21 in its flat, uncontracted state, with the exterior portion of the diaper 20 that faces outwardly away from the wearer shown facing the viewer.

For example, as shown in FIG. 21 and FIG. 22, laterally opposing adhesive tape tabs 114a and 114b may be attached to the chassis 100 at or adjacent to the side edges 137a and 137b of the diaper 20. The adhesive tape tabs 114a and 114b shown in FIG. 21 and FIG. 22 project laterally outward from the respective side edges 137a and 137b in the back waist region 38. In use, the adhesive tape tabs 114a and 114b shown in FIG. 21 and FIG. 22 may be adhered to the exterior surface 104 of the chassis 100 in the front waist region 36 to fasten the back waist region 38 to the front waist region 36 in a back-over-front manner. Alternatively, similar adhesive tape tabs may be attached to the chassis 100 in the front waist region 36 and used to fasten the front waist region 36 to the back waist region 38 in a front-over-back manner. Suitable adhesive tapes are available from the 3M Corporation of St. Paul, Minn., U.S.A., under the designation of XMF99121.

Each of the adhesive tape tabs may be formed of two or more layers and different ones of these layers may be attached to different surfaces of the chassis. For example, as shown in FIG. 21 and FIG. 22, an interior layer 114c of the left adhesive tape tab 114a is attached onto the left side flap 147a, while an exterior layer 114d of the left adhesive tape tab 114a is attached onto the exterior surface 104 of the chassis 100. Similarly, an interior layer 114e of the right adhesive tape tab 114b is attached onto the right side flap 147b, while an exterior layer 114f of the right adhesive tape tab 114b is attached onto the exterior surface 104 of the chassis 100. This form of attachment of adhesive tape tabs to the chassis provides the advantage that each of the interior layer and the exterior layer of each adhesive tape tab is subjected essentially to only a shear force at its attachment to the chassis, rather than being subjected to both shear and peel forces. For example, any tendency of the interior layer 114c to peel off of the left side flap 147a is counteracted by the exterior layer 114d acting in tension to prevent the interior layer 114c from peeling off. Conversely, any tendency of the exterior layer 114d to peel off of the exterior surface 104 of the chassis 100 is counteracted by the interior layer 114c acting in tension to prevent the exterior layer 114d from peeling off. The exterior layers of the adhesive tape tabs shown in FIG. 21 and FIG. 22 extend farther toward the longitudinal axis than do the interior layers of the adhesive tape tabs. Alternatively, the interior layers may extend farther toward the longitudinal axis than the exterior layers, or both layers may extend equally far toward the longitudinal axis. If the materials onto which the layers of the adhesive tape tab differ in tensile strength or if the attachment of the adhesive tape tab is relatively more secure on one of the surfaces, it may be desirable that the layer that is attached to the stronger material or that is more securely attached to the surface extend farther toward the longitudinal axis in order to distribute the force carried by the adhesive tape tab disproportionately onto the stronger material or the more secure attachment.

Optionally, a fastening sheet 116 may be attached onto the exterior surface 104 of the chassis 100 in the front waist region 36 as shown in FIG. 21 and FIG. 22. The fastening sheet 116 shown in FIG. 21 and FIG. 22 lies entirely inside the edges of the diaper 20. Alternatively, two or more discrete fastening sheets may be attached onto the exterior surface of the chassis, instead of a single fastening sheet. For example, two laterally opposing fastening sheets may be attached in locations approximately corresponding to the left and right portions of the single fastening sheet 116. When a fastening sheet is provided, the adhesive tape tabs may be adhered to the fastening sheet to fasten the back waist region 38 and the front waist region 36 together. The fastening sheet may be formed of a material used elsewhere in the diaper, such as a film or a nonwoven. In embodiments in which the chassis is extensible, it is preferred that any fastening sheet also be extensible such that the fastening sheet will not restrict the extensibility of the portion of the chassis onto which it is attached. For example, an extensible nonwoven may be used for the fastening sheet. The fastening sheet serves to distribute the tensile force transmitted by each of the adhesive tape tabs over an area of the backsheet 26 that is larger than the adhered area of the adhesive tape tab. In addition, when a single fastening sheet such as fastening sheet 116 in FIG. 21 and FIG. 22 is used, the fastening sheet may, itself, bear a portion of the tensile force between the laterally opposing adhesive tape tabs and thereby relieve a portion of the force exerted on the backsheet. Thus, the incorporation of such a fastening sheet may be desirable, for example, in order to make it possible to use a relatively inexpensive and relatively weak material for the backsheet 26. The fastening sheet may be formed of a material having greater strength than the backsheet. Such a stronger material may be more expensive per unit area than the backsheet, but the fastening sheet may be relatively smaller than the backsheet. Therefore, the total cost of a diaper having a fastening sheet may be less than the total cost of a diaper having a backsheet having sufficient strength for adhesive tape tabs to be adhered directly to the exterior surface of the backsheet.

Exemplary fastening elements in the form of cohesive fastening patches are described in this application and the description of their disposition, configuration, and use is intended to apply to any other type of incorporated fastening element insofar as is practical for each such type of fastening element.

Exemplary fastening elements in the form of cohesive fastening patches may be formed of an inherently crystalline water-based synthetic elastomer to which a tackifying agent has been added to disrupt the polycrystalline structure and thereby render the elastomer cohesive. Such synthetic cohesive products are available from Andover Coated Products, Incorporated, of Salisbury, Mass., U.S.A. and are described in U.S. Pat. No. 6,156,424 issued on 5 Dec. 2000 in the name of Taylor. A cohesive elastomeric fastening element preferably remains extensible in use. Thus, when applied onto an extensible chassis, such a cohesive elastomeric fastening element may be capable of extending as the extensible chassis extends. As a result, when subjected to the tensile hoop forces typically found at the waist opening of a diaper when the diaper is worn, the area of attachment of two cohesive elastomeric fastening elements to each other may be subject only to a shearing force, rather than being subjected to a peeling force. This behavior may enable the fastening elements to remain cohered even when they are extended because cohesive fastening elements typically exhibit relatively higher resistance to shearing forces than to peeling forces.

Cohesive fastening patches may be formed by the application of a cohesive material directly onto the chassis or onto a separate substrate that is in turn attached to the chassis. For example, a "hot melt" cohesive material may be applied in its molten state onto a surface and allowed to cool and solidify to form such a patch. The cohesive material may be applied in any of a variety of patterns, such as a continuous film, discrete dots, stripes, polygons, etc., and/or spaced and interconnected geometric elements describing a grid.

Figure 23:
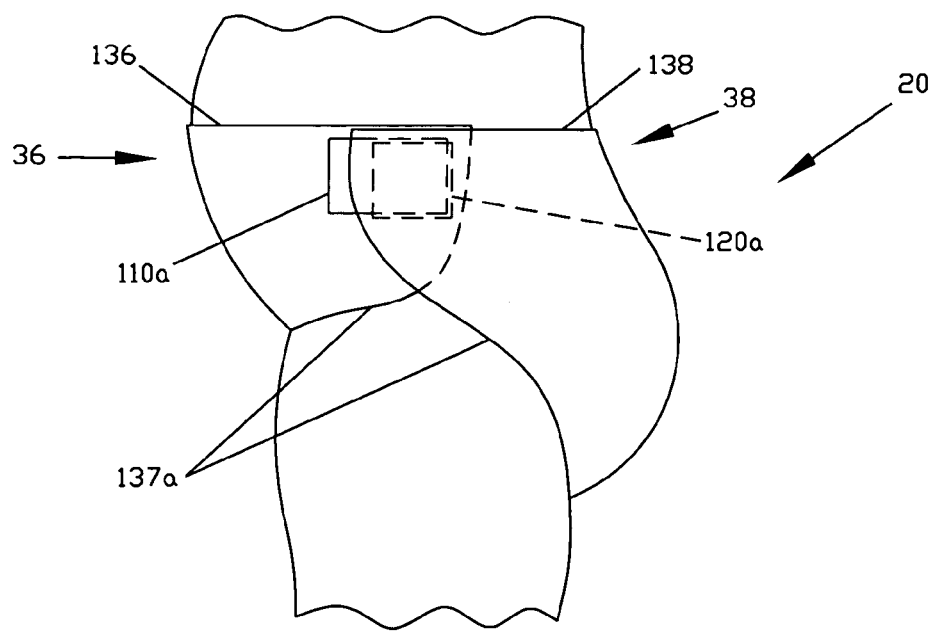
FIG. 23 is a simplified left side elevation view of an exemplary diaper 20 including cohesive fastening patches being worn about a lower torso of a wearer.
Figure 24:
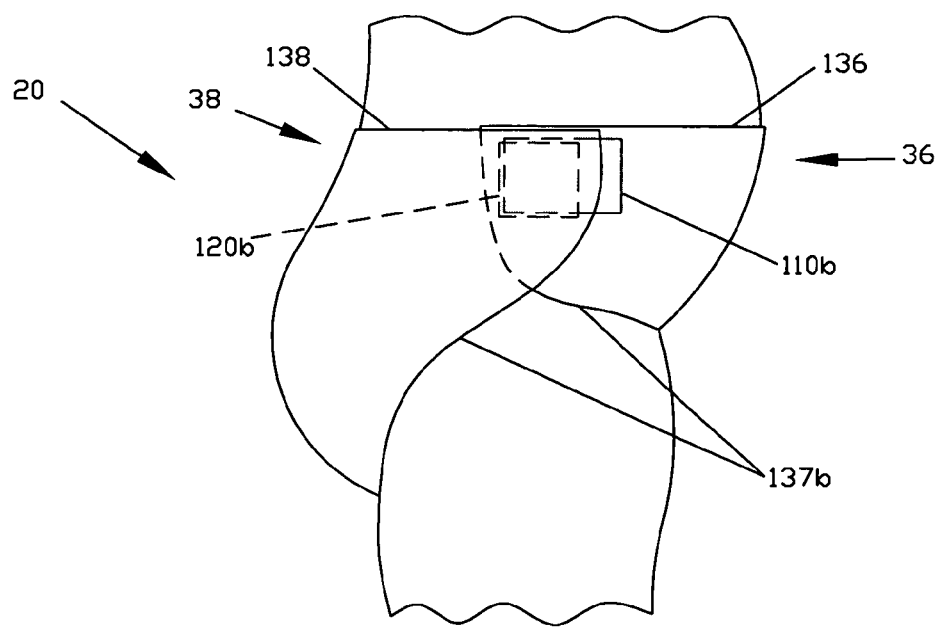
FIG. 24 is a simplified right side elevation view of the diaper 20 of FIG. 23 including cohesive fastening patches being worn about the lower torso of the wearer.
Figure 25:
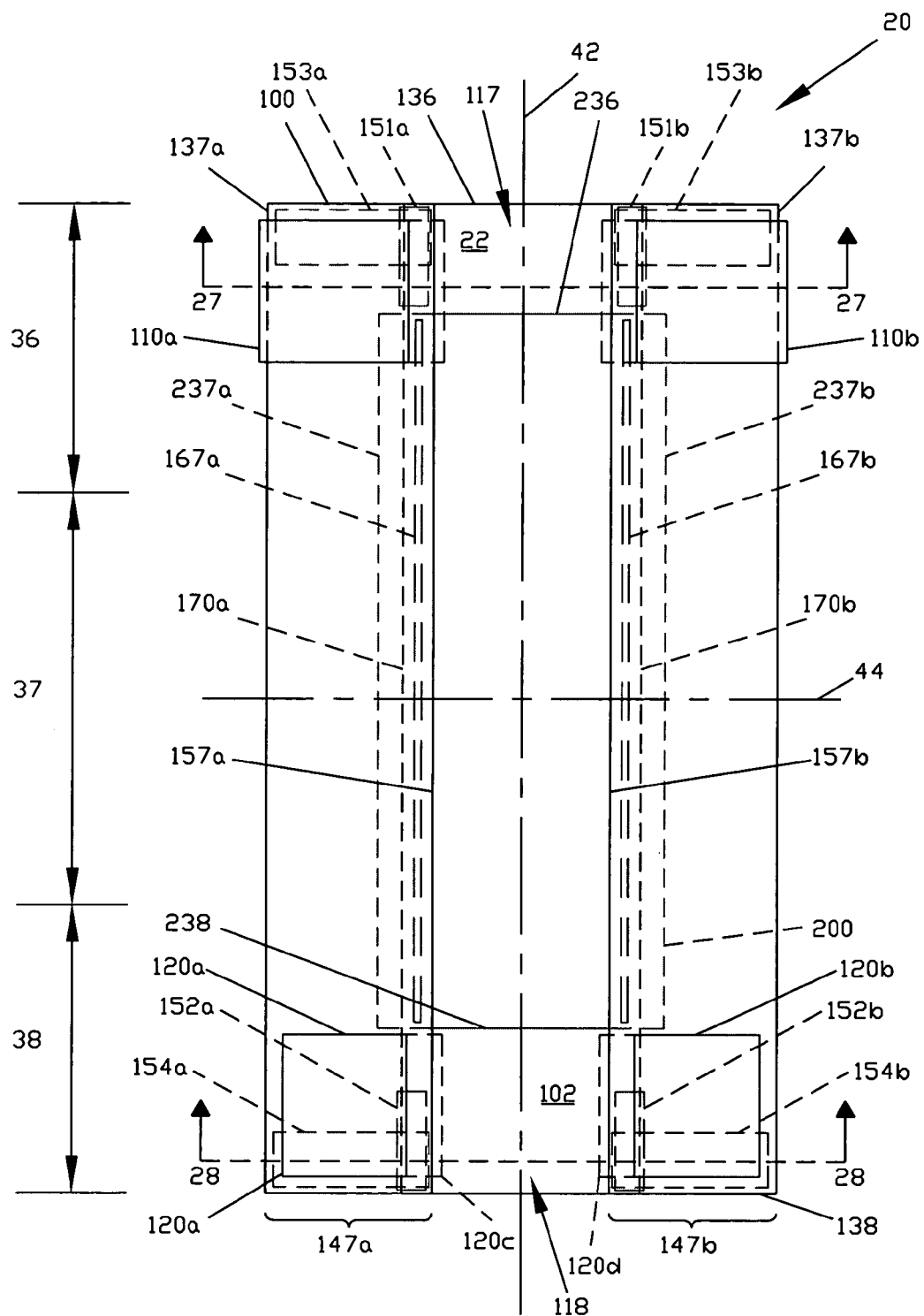
FIG. 25 is a plan view of an exemplary diaper 20 shown in its flat, uncontracted state, i.e., without the contraction induced by elastic members, in which alternative forms of cohesive fastening patches are shown incorporated.
Figure 26:
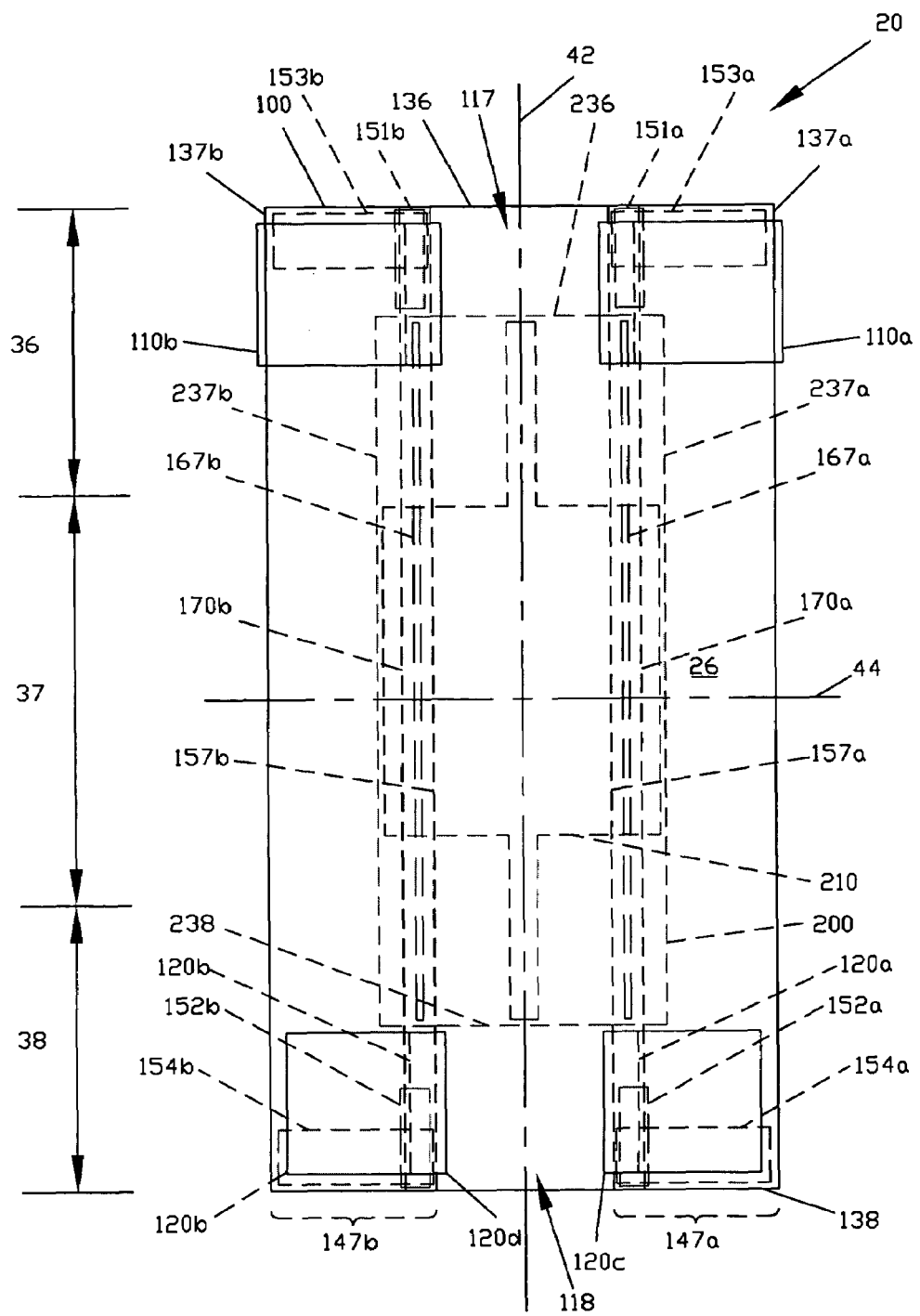
FIG. 26 is a plan view of the diaper 20 of FIG. 25 in its flat, uncontracted state, with the exterior portion of the diaper 20 that faces outwardly away from the wearer shown facing the viewer.
Figure 27:
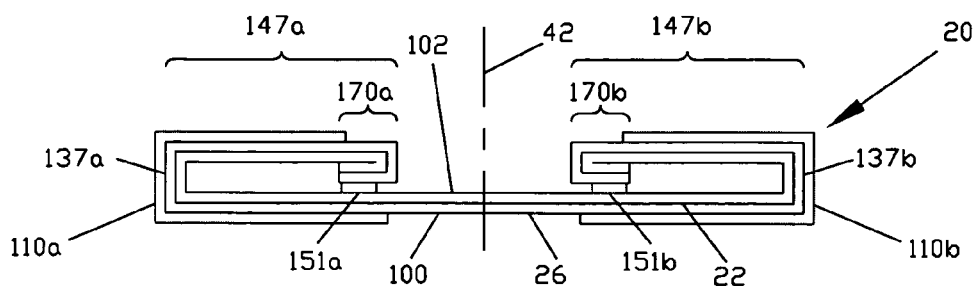
FIG. 27 is a section view of the diaper 20 of FIG. 25 taken at the section line 27-27.
Figure 28:
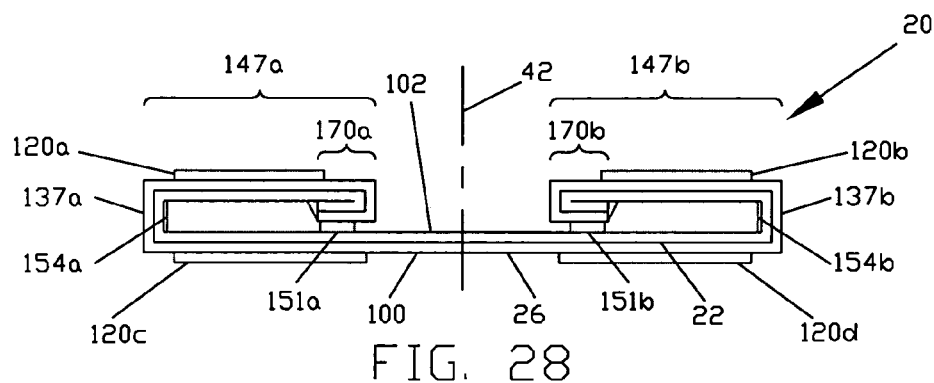
FIG. 28 is a section view of the diaper 20 of FIG. 25 taken at the section line 28-28.

Exemplary cohesive fastening patches are shown incorporated into the chassis in FIG. 1, FIG. 2, FIG. 3, FIG. 6, FIG. 10, FIG. 11, FIG. 12, FIG. 15, FIG. 23, and FIG. 24. In these exemplary embodiments, a cohesive fastening patch 110a is disposed on the exterior of the chassis 100 in the front waist region 36 adjacent to the left side edge 137a and a laterally opposing cohesive fastening patch 110b is disposed on the exterior of the chassis 100 in the front waist region 36 adjacent to the right side edge 137b. A cohesive fastening patch 120a is disposed on the interior of the chassis 100 in the back waist region 38 adjacent to the left side edge 137a and a laterally opposing cohesive fastening patch 120b is disposed on the interior of the chassis 100 in the back waist region 38 adjacent to the right side edge 137b. When the diaper 20 is worn as shown in FIG. 23 and FIG. 24, the back left cohesive fastening patch 120a overlaps the front left cohesive fastening patch 110a and the cohesion of these two cohesive fastening patches fastens the front waist region 36 and the back waist region 38 together at the left side of the diaper 20. Similarly, the back right cohesive fastening patch 120b overlaps the front right cohesive fastening patch 110b and the cohesion of these two cohesive fastening patches fastens the front waist region 36 and the back waist region 38 together at the right side of the diaper 20. Thus, the configuration of the cohesive fastening patches shown in these figures is adapted for back-over-front fastening. Alternatively, the front cohesive fastening patches may be disposed on the interior of the chassis in the front waist region and the back cohesive fastening patches may be disposed on the exterior of the chassis in order to adapt the configuration of the cohesive fastening patches for front-over-back fastening. In FIG. 23 and FIG. 24, the cohesive fastening patches are shown overlapped but not exactly aligned along any of their respective edges only for clarity of illustration and can actually be aligned as desired, e.g., to maximize their areas of overlap.

Alternatively, the cohesive fastening patches may be disposed in a reversible configuration that is adapted to provide the user of the diaper 20 with both options for fastening, i.e., either back-over-front or front-over-back, according to personal preference. When the cohesive fastening patches are disposed on both the exterior and the interior of the chassis 100, a back cohesive fastening patch may overlap a front cohesive fastening patch or the front cohesive fastening patch may overlap the back cohesive fastening patch and, in either arrangement, the cohesive fastening patches fasten the front waist region 36 and the back waist region 38 together at the side of the diaper 20. Thus, with this configuration of the cohesive fastening patches, the fastening of the diaper 20 at the sides is reversible so that each side can be fastened in a back-over-front manner or, alternatively, in a front-over-back manner.

Two such reversible configurations of cohesive fastening patches are shown in FIG. 25, FIG. 26, FIG. 27, and FIG. 28. In the first of these exemplary configurations, a cohesive fastening patch 110a wraps around the left side edge 137a and is disposed on both the exterior and the interior of the chassis 100 in the front waist region 36 adjacent to the left side edge 137a. A laterally opposing cohesive fastening patch 110b wraps around the right side edge 137b and is disposed on both the exterior and the interior of the chassis 100 in the front waist region 36 adjacent to the right side edge 137b. Such a continuous configuration may be desirable, for example, in order to allow the cohesive polymer for each cohesive fastening patch to be applied in a single area that is then folded over when the corresponding folded side flap is formed in a manufacturing process.

In the second exemplary reversible configuration of the cohesive fastening patches, a pair of back cohesive fastening patches 120a and 120b do not extend around the side edges 137a and 137b and thus are not continuous from the exterior to the interior of the chassis 100. Instead, a back left interior cohesive fastening patch 120a and a back left exterior cohesive fastening patch 120c are disposed on the respective interior and exterior of the chassis 100 adjacent to the left side edge 137a in the back waist region 38. Similarly, a back right interior cohesive fastening patch 120b and a back right exterior cohesive fastening patch 120d are disposed on the respective interior and exterior of the chassis 100 adjacent to the right side edge 137b in the back waist region 38. Such a discontinuous configuration may be desirable, for example, in order to allow the cohesive polymer to be applied after the side flaps are formed in a manufacturing process. In general, any or all of the cohesive fastening patches may extend around the side edges 137a and 137b or may be discontinuous from the exterior to the interior of the chassis 100.

As an alternative to overlapping cohesive fastening patches to fasten the front waist region 36 and the back waist region 38 together to encircle the waist and the legs of the wearer, the fastening patches may be disposed on the interior surface of the chassis and may be abutted in a face-to-face arrangement to form a flanged connection in which, for example, a portion of the side edge 137a in the back waist region and a portion of the same side edge 137a in the front waist region are superposed, i.e., unlike an overlapped connection, both of the portions of the side edge are exposed in such a flanged connection.

The exemplary diapers shown in FIG. 1, FIG. 2, FIG. 3, FIG. 6, FIG. 10, FIG. 11, FIG. 12, FIG. 15, FIG. 23, and FIG. 24 include discrete laterally opposing cohesive fastening patches. Alternatively, a single laterally extending cohesive fastening patch may be attached at each of the longitudinally opposing waist regions of the diaper. For example, each such single cohesive fastening patch may extend laterally to approximately the lateral extent that is defined by the laterally distal edges of the discrete cohesive fastening patches shown in these figures. Thus, such a single cohesive fastening patch may have approximately the same extent and be located in approximately the same location as the fastening sheet 116 shown in FIG. 21 and FIG. 22.

Description of the Absorbent Assembly

Figure 29:
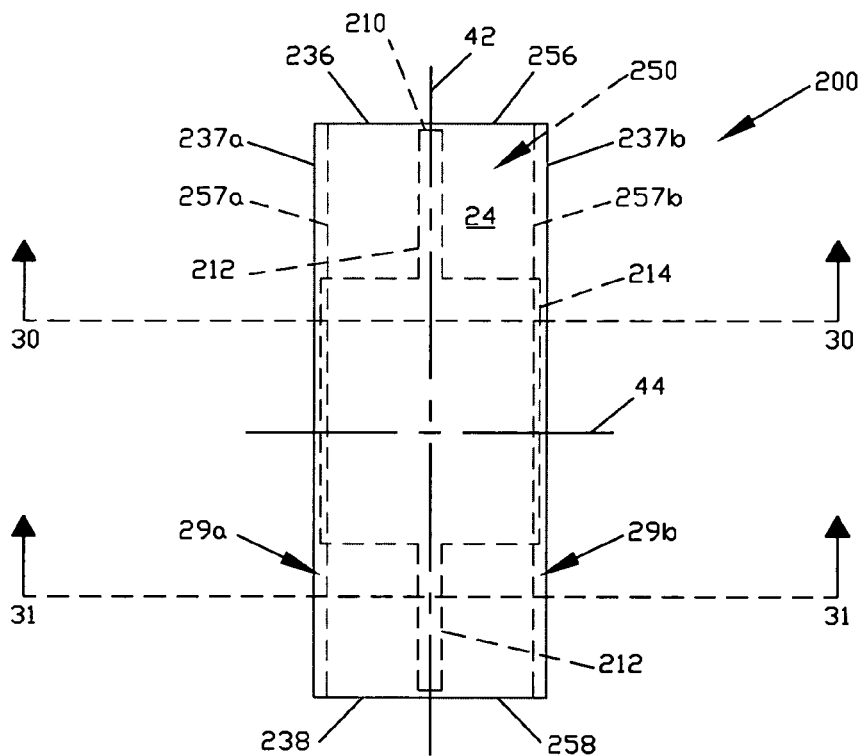
FIG. 29 is a plan view of an exemplary absorbent assembly 200.
Figure 30:
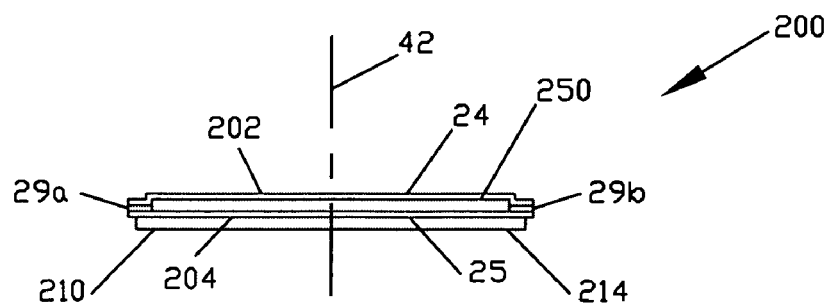
FIG. 30 is a section view of the absorbent assembly 200 of FIG. 29 taken at the section line 30-30.
Figure 31:
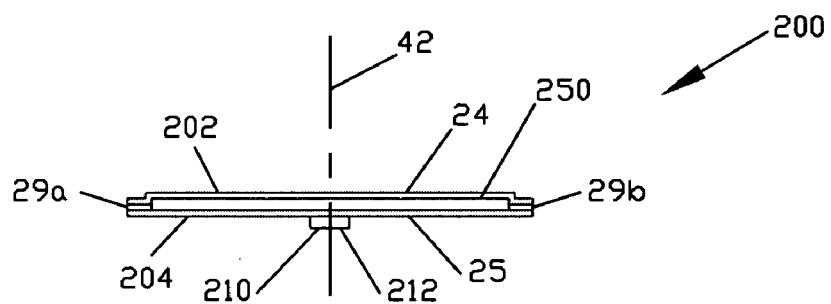
FIG. 31 is a section view of the absorbent assembly 200 of FIG. 29 taken at the section line 31-31.

As shown in FIG. 29, FIG. 30, and FIG. 31, the absorbent assembly 200 includes an absorbent core 250. The absorbent core 250 has a laterally extending front edge 256 in the front waist region 36 and a longitudinally opposing and laterally extending back edge 258 in the back waist region 38. The absorbent core 250 also has a longitudinally extending left side edge 257a and a laterally opposing and longitudinally extending right side edge 257b, both absorbent core side edges extending longitudinally between the front edge 256 and the back edge 258. Any or all of the respective front edge 256, back edge 258, left side edge 257a, and right side edge 257b of the absorbent core 250 may lie inward of the respective front edge 236, back edge 238, left side edge 237a, and right side edge 237b of the absorbent assembly 200. For example, in the exemplary absorbent assembly 200 shown in FIG. 29, the absorbent core 250 has its left side edge 257a and right side edge 257b located laterally inward of, respectively, the left side edge 237a and right side edge 237b of the absorbent assembly 200. Alternatively, one or more of the edges of the absorbent core 250 may coincide with the corresponding edge of the absorbent assembly 200. For example, in the exemplary absorbent assembly 200 shown in FIG. 29, the front edge 256 and back edge 258 of the absorbent core 250 coincide with the respective front edge 236 and back edge 238 of the absorbent assembly 200.

The absorbent assembly 200 may be attached to the chassis 100 over any part or the whole of the area of the absorbent assembly 200. Preferably, the absorbent assembly 200 is attached on its exterior surface 204 to the chassis 100 in a cruciform attachment pattern, i.e., in an attachment pattern that forms or is arranged in a cross or "+" shape. The cruciform attachment pattern may be contiguous, i.e., all of its portions may be touching or connected throughout the pattern in an unbroken sequence. Alternatively, the cruciform attachment pattern may include detached portions and thereby lack contiguity but still be arranged such that the shape of the overall pattern is a cruciform. For example, a discontiguous cruciform attachment pattern may include a longitudinally extending portion disposed along the longitudinal axis and separate left and right laterally distal portions disposed along or adjacent to the lateral axis and thereby form a cruciform as the shape of the overall pattern.

An exemplary contiguous cruciform attachment pattern 210 is shown in FIG. 26, FIG. 29, FIG. 30, and FIG. 31. The portions of the chassis 100 that lie outside such a cruciform attachment pattern are not restrained by attachment to the absorbent assembly 200 and therefore remain extensible. In particular, a relatively narrow longitudinally extending portion 212 of a cruciform attachment pattern 210 like that shown in FIG. 29 and FIG. 31 leaves the majority of the width of the chassis 100 in the front waist region 36 and in the back waist region 38 freely extensible and thereby allows extension of the chassis 100 in the lateral direction in these regions. A relatively wide laterally extending portion 214 of a cruciform attachment pattern 210 like that shown in FIG. 29 and FIG. 30 prevents the portion of the chassis 100 in the crotch region 37 to which the absorbent assembly 200 is attached from shifting relative to the absorbent assembly 200 in that region. A relatively wide laterally extending portion 214 of a cruciform attachment pattern 210 may also contribute to the effectiveness of the side flaps 147a and 147b when the elastic strands 167a and 167b lift the proximal edges 157a and 157b into contact with the body of the wearer. For example, if the chassis 100 in the crotch region 37 were free to shift laterally inward, i.e., toward the longitudinal axis 42 such that the left side edge 137a and/or the right side edge 137b moved toward the longitudinal axis 42, the side flaps 147a and 147b might easily distort and fail to maintain contact with the body. However, because the relatively wide laterally extending portion 214 of the cruciform attachment pattern 210 restrains the chassis 100 over a relatively wide portion of the width of the crotch region 37, the side flaps 147a and 147b are better supported at their bases while being lifted by the elastic strands 167a and 167b.

The cruciform attachment pattern 210 in FIG. 29, FIG. 30, and FIG. 31 extends laterally from near the left side edge 237a to near the right side edge 237b of the absorbent assembly 200 at and adjacent to the lateral axis 44, but does not extend laterally to this extent over the full length of the absorbent assembly 200. Similarly, the cruciform attachment pattern 210 in FIG. 29, FIG. 30, and FIG. 31 extends longitudinally from near the front edge 236 to near the back edge 238 of the absorbent assembly 200 at and adjacent to the longitudinal axis 42, but does not extend longitudinally to this extent over the full width of the absorbent assembly 200. Alternatively, the cruciform attachment pattern 210 may extend to any or all of the side edges 237a and 237b and the front edge 236 and the back edge 238 of the absorbent assembly 200. For example, the cruciform attachment pattern 210 may extend laterally from the left side edge 237a to the right side edge 237b of the absorbent assembly 200, but may extend longitudinally only a part of the distance from the front edge 236 to the back edge 238 of the absorbent assembly 200. Within the extent of the cruciform attachment pattern 210, the absorbent assembly 200 may be attached to the chassis 100 continuously or intermittently. For example, a film of an adhesive may be applied continuously over the entire area of the cruciform attachment pattern and then used to continuously attach the absorbent assembly to the chassis. As an alternative example, an adhesive may be applied discontinuously at and inside the boundaries of the cruciform attachment pattern, such as in the form of dots, stripes, beads, spirals, etc., and then used to attach the absorbent assembly to the chassis.

The cruciform attachment pattern 210 may be disposed symmetrically with respect to either or both of the longitudinal axis 42 and the lateral axis 44 of the chassis 100. Alternatively, the cruciform attachment pattern 210 may be disposed asymmetrically with respect to either or both of the longitudinal axis 42 and the lateral axis 44. For example, the cruciform attachment pattern 210 shown in FIG. 29 is disposed symmetrically with respect to the longitudinal axis 42 and asymmetrically with respect to the lateral axis 44. In particular, the cruciform attachment pattern 210 shown in FIG. 29 is disposed asymmetrically toward the front waist region 36. Also, the laterally extending portion 214 of the cruciform attachment pattern 210 may be located distant from the lateral axis 44 and the longitudinally extending portion 212 of the cruciform attachment pattern 210 may similarly be located distant from the longitudinal axis 42. In addition, the cruciform attachment pattern 210 may be disposed symmetrically with respect to either or both of the side edges 237a and 237b and the front edge 236 and the back edge 238 of the absorbent assembly 200. For example, the cruciform attachment pattern 210 shown in FIG. 29 is disposed symmetrically with respect to both the side edges 237a and 237b and the front edge 236 and the back edge 238, i.e., the cruciform attachment pattern 210 shown in FIG. 29 is centered on the absorbent assembly 200. Alternatively, the cruciform attachment pattern 210 may be disposed asymmetrically with respect to either or both of the side edges 237a and 237b and front edge 236 and back edge 238 of the absorbent assembly 200, i.e., the cruciform attachment pattern 210 may be disposed off-center on the absorbent assembly 200.

The absorbent core 250 may be disposed between a lower covering sheet that is disposed on the exterior face of the absorbent core 250 in a face-to-face arrangement with the interior surface 102 of the chassis and an upper covering sheet that is disposed on the interior face of the absorbent core 250. Such an upper covering sheet and lower covering sheet may be attached together to contain the absorbent core 250 between them and thereby form the absorbent assembly 200. For example, in the exemplary absorbent assembly 200 shown in FIG. 29, FIG. 30, and FIG. 31, an upper covering sheet 24 and a lower covering sheet 25 are attached together at or adjacent to the side edges 237a and 237b of the absorbent assembly 200 in longitudinally extending adhesive attachment zones 29a and 29b. Alternatively, the upper covering sheet 24 and the lower covering sheet 25 may be attached together in places other than the side edges 237a and 237b of the absorbent assembly 200, e.g., at or adjacent to the end edges 236 and 238 of the absorbent assembly 200, or at or adjacent to both the end edges 236 and 238 and the side edges 237a and 237b.

The upper covering sheet 24 is water-permeable and allows liquid waste to pass through to the absorbent core 250, where the liquid waste is absorbed. The lower covering sheet 25 may be water-impermeable. However, the lower covering sheet 25 preferably is water-permeable. In embodiments in which both the upper covering sheet 24 and the lower covering sheet 25 are water-permeable, any liquid waste that is deposited onto the upper covering sheet 24 but does not pass through the upper covering sheet 24 to the absorbent core 250 can flow around an edge of the absorbent assembly 200 to reach the lower covering sheet 25 and then pass through the lower covering sheet 25 to the absorbent core 250.

The upper covering sheet 24 may form the interior surface 202 of the absorbent assembly 200 that is intended to be placed against the body of the wearer. The upper covering sheet 24 preferably is formed of a soft material that will not irritate the skin of the wearer. Many materials that are suitable for a water-permeable covering sheet are well-known in the art, including synthetic nonwovens such as spunbonded or carded polypropylene, polyester, or rayon. Likewise, many materials that are suitable for a covering sheet that is water-impermeable are well-known in the art, including the materials that are suitable for the backsheet 26.

The upper covering sheet 24 and the lower covering sheet 25 may extend to the same width and the same length. Alternatively, one or more of the edges of one of the covering sheets may lie distally relative to the respective edge or edges of the other covering sheet. For example, the upper covering sheet may extend longitudinally only to an extent sufficient to cover the absorbent core and the lower covering sheet may extend longitudinally beyond the upper covering sheet toward or to the adjacent waist edge. Such an extended covering sheet may serve to isolate the skin of the wearer from a portion of the backsheet 26 as may be desirable, for example, when the diaper 20 is worn under conditions in which contact between the skin and a backsheet film could be uncomfortable.

Suitable absorbent materials for the absorbent core are well-known, including cellulose fibers in the form of comminuted wood pulp, which is commonly known as "airfelt", layers or sheets of natural or synthetic fibrous material, superabsorbent polymer, etc. These absorbent materials may be used separately or in combination. Many known absorbent materials may be used in a discrete form, i.e., in the form of fibers, granules, particles, and the like. Such a discrete form of an absorbent material may be immobilized by an adhesive that attaches the discrete pieces together to form a coherent layer or that attaches the discrete pieces to a substrate layer, such as a covering sheet, or that attaches the discrete pieces both to each other and to the substrate layer.

Figure 32:
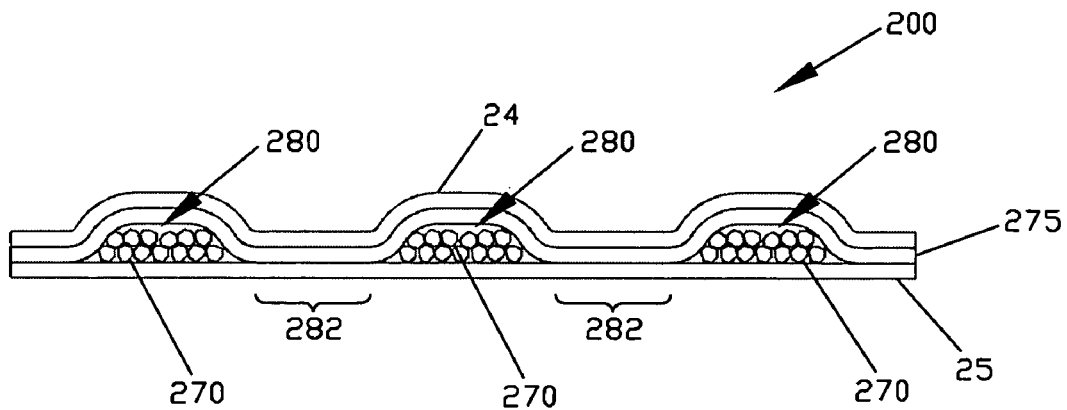
FIG. 32 is a section view of an exemplary absorbent assembly 200 showing details of an exemplary absorbent core.

Alternatively, the discrete form of an absorbent material may be immobilized in pockets formed by a layer of a thermoplastic material, such as a hot melt adhesive, that intermittently contacts and adheres to a substrate, such as a covering sheet, while diverging away from the substrate at the pockets. Absorbent assemblies having such structures are described in U.S. Patent Application Publications Nos. 2004/0162536 of 19 Aug. 2004 and 2004/0167486 of 26 Aug. 2004. An exemplary absorbent assembly 200 having such a structure is shown in FIG. 32. In this absorbent assembly 200, the absorbent core 250 includes particles of superabsorbent polymer 270 that are contained inside pockets 280 formed by a layer 275 of a thermoplastic material. This absorbent core 250 contains no cellulose fibers. Alternatively, the absorbent core 250 may include both particles of superabsorbent polymer and airfelt and both materials may be contained inside the pockets formed by the layer of the thermoplastic material. As shown in FIG. 32, the layer 275 of the thermoplastic material intermittently contacts and adheres to the lower covering sheet 25 at the areas of attachment 282. Between the areas of attachment 282, the layer 275 diverges away from the lower covering sheet 25 to form the pockets 280. The layer 275 may have the form of a sheet of fibers of the thermoplastic material through which the liquid waste may pass to the particles of superabsorbent polymer 270 to be absorbed.

In FIG. 32, a separate upper covering sheet 24 is shown overlying the layer 275 of the thermoplastic material. Alternatively, the separate upper covering sheet 24 may be omitted and the layer 275 in the form of a fibrous sheet may serve as the upper covering sheet 24. As another alternative, two absorbent assemblies each like that shown in FIG. 32 except for the omission of the upper covering sheet 24 may be superposed with one absorbent assembly inverted such that its pockets nest into the recesses at the areas of attachment 282 of the other absorbent assembly and the respective single covering sheets distally oppose each other. In such a combined absorbent assembly 200, the distally opposing single covering sheets may serve respectively as the upper covering sheet 24 and the lower covering sheet 25.

In the exemplary absorbent assembly 200 shown in FIG. 29, FIG. 30, and FIG. 31, the upper covering sheet 24 and the lower covering sheet 25 are of the same size, i.e., both the upper covering sheet 24 and the lower covering sheet 25 extend to the front edge 236 and back edge 238, as well as to the left side edge 237a and right side edge 237b of the absorbent assembly 200. Alternatively, the upper covering sheet 24 and the lower covering sheet 25 may differ in size. For example, the lower covering sheet 25 may be larger than the upper covering sheet 24 and may be wrapped over the side edges 257a and 257b of the absorbent core 250 onto the interior surface of the absorbent core 250, where the upper covering sheet 24 and the lower covering sheet 25 may be attached together. Alternatively, in place of a separate upper covering sheet 24 and a separate lower covering sheet 25, a single covering sheet may be wrapped around the absorbent core 250 and attached to itself to contain the absorbent core 250. Such a single covering sheet forms an upper layer and a lower layer when wrapped around the absorbent core 250 and, in general, the description of the separate upper covering sheet 24 and lower covering sheet 25 are intended to apply to such upper and lower layers of a wrapped single covering sheet.

At a minimum, the absorbent core 250 is contained laterally by the covering sheet or sheets being wrapped around the absorbent core 250 or attached together at or adjacent to the left side edge 237a and right side edge 237b of the absorbent assembly 200. For example, in the exemplary absorbent assembly 200 shown in FIG. 29, FIG. 30, and FIG. 31, the upper covering sheet 24 and the lower covering sheet 25 are attached together only in left adhesive attachment zone 29a and right adhesive attachment zone 29b at or adjacent to the respective left side edge 237a and right side edge 237b of the absorbent assembly 200. In this embodiment, the upper covering sheet 24 and the lower covering sheet 25 cannot be attached directly together at or adjacent to the front edge 236 and back edge 238 because the absorbent core 250 extends the full length of the absorbent assembly 200, i.e. the front edge 256 and back edge 258 of the absorbent core 250 coincide with the respective front edge 236 and back edge 238 of the absorbent assembly 200. In such an embodiment, the upper and lower layers of the covering sheet or sheets may each be attached to the absorbent core 250 at or adjacent to the front edge 256 and back edge 258 of the absorbent core 250 to form a sandwich. In addition, a sealing agent may be applied at or adjacent to the front edge 256 and back edge 258 of the absorbent core 250 to contain any fibers or particles that might otherwise escape the absorbent core 250. Alternatively, instead of being contained only laterally by the covering sheet or sheets, the absorbent core 250 may additionally be contained longitudinally by the upper and lower layers of the covering sheet or sheets being attached together at or adjacent to the front edge 236 and back edge 238 of the absorbent assembly 200.

STATEMENTS OF INCORPORATION BY REFERENCE AND INTENDED SCOPE OF CLAIMS

The disclosures of all patents, patent applications and any patents which issue thereon, as well as any corresponding published foreign patent applications, and all publications listed and/or referenced in this description, are hereby incorporated herein by reference. It is expressly not admitted that any of the documents or any combination of the documents incorporated herein by reference teaches or discloses the present invention.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A disposable diaper comprising:
 a web comprising and an interior surface and an exterior surface and forming multiple components of the diaper, including a front waist region, a back waist region, a crotch region between the front and back waist regions, a front waist edge, a back waist edge, laterally opposing side edges, a backsheet, and barrier leg cuffs;
 a longitudinal axis extending from a midpoint of the front waist edge through the crotch region to a midpoint of the longitudinally opposed back waist edge;
 one or more fasteners attached to the exterior surface of the web in one or more of the front and back waist regions;
 an absorbent assembly attached directly to the interior surface of the web; and
 wherein a portion of the web disposed in both the front and back waist regions is inwardly folded and bonded to one of the interior surface of the web and interior surface of the absorbent assembly at or adjacent the waist end edges to form first and second laterally opposing side flaps, the first and second side flaps each comprising a distal folded edge extending longitudinally and a laterally opposing longitudinally extending proximal edge, the proximal edges of the first and second side flaps being disposed laterally inward of the respective distal folded edges, wherein the inwardly folded first and second side flaps comprise first and second proximal free edges of the first and second side flaps, respectively, disposed between longitudinally opposed bonds, a portion of the web being folded laterally outward to contain first and second longitudinally extending elastic gathering members, respectively.

2. A disposable diaper comprising:
- a front waist region, a back waist region, a crotch region between the waist regions, a front waist edge, and a back waist edge;
- a longitudinal axis extending from a midpoint of the front waist edge through the crotch region to a midpoint of the longitudinally opposed back waist edge;
- a web comprising an interior surface and an exterior surface;
- an absorbent assembly comprising an interior surface and an exterior surface;
- wherein the web is folded laterally outward over at a first fold line and attached to itself interior surface to interior surface forming a first hem and a proximal edge;
- wherein the web is folded laterally outward over at a second fold line and attached to itself interior surface to interior surface forming a second hem;
- wherein the web is folded laterally inward over at a third fold line and attached to the interior surface of one or both of the web and absorbent assembly in the front and back waist regions forming a first side flap, the third fold line forming a first side edge of the diaper;
- wherein the web is folded laterally inward over at a fourth fold line and attached to the interior surface of one or both of the web and absorbent assembly in the front and back waist regions forming a second side flap, the fourth fold line forming a second side edge of the diaper;
- wherein the first side flap comprises the first hem and wherein the second side flap comprises the second hem;
- wherein each of the first and second hems comprise a longitudinally extending gathering member; and
- wherein the proximal edges of the first and second side flaps are disposed laterally inward of the respective side edges.

3. The disposable diaper of claim 2 wherein the web comprises altered and unaltered regions, and wherein the altered region of the web is formed by deformation.

4. The disposable diaper of claim 3 wherein the altered region of the web comprises a pattern of alternating ridges and valleys created by a deformation.

5. The disposable diaper of claim 4 wherein the ridges and valleys are generally longitudinally oriented.

6. The disposable diaper of claim 3 wherein the web comprises an altered region in at least one of the waist regions.

7. The disposable diaper of claim 6 wherein at least a portion of the web in one of the waist regions is laterally extensible to a maximum extensibility greater than a maximum extensibility of at least a portion of the web in the crotch region.

8. The disposable diaper of claim 2 wherein the side flaps are attached to the interior surface of the web in laterally opposing attachment zones immediately adjacent to the first and second side edges of the diaper, respectively.

9. The disposable diaper of claim 8 wherein the laterally opposing attachment zones are comprised in the front and back waist regions.

10. The disposable diaper of claim 9 wherein the laterally opposing attachment zones are immediately adjacent to the first and second side edges of the diaper, and are immediately adjacent to front and back edges of the diaper.

11. The disposable diaper of claim 2 wherein fastening elements for fastening the front waist region to the back waist region to encircle a waist and a leg of a wearer are attached to the web.

12. The disposable diaper of claim 11 wherein the fastening elements include at least one fastening sheet attached to the exterior surface of the web.

13. The disposable diaper of claim 11 wherein the fastening elements comprise mechanical fastening elements.

14. The disposable diaper of claim 2 wherein the absorbent assembly includes a water-permeable covering sheet and an absorbent core, wherein the covering sheet is disposed on an interior face of the absorbent core and the absorbent assembly, and wherein the absorbent assembly also includes a second water-permeable covering sheet disposed on an exterior face of the absorbent core.

15. The disposable diaper of claim 2 wherein the absorbent assembly is attached to the interior surface of the web.

16. The disposable diaper of claim 2 wherein the absorbent assembly is attached to the web via an attachment pattern comprising a longitudinally extending portion disposed along the longitudinal axis and at least one laterally distal portion.

17. The disposable diaper of claim 16 wherein the attachment pattern is discontiguous.

18. The disposable diaper of claim 2 wherein the absorbent assembly is attached to the web via a discontiguous attachment pattern.

19. The disposable diaper of claim 18 wherein the attachment pattern comprises a longitudinally extending portion disposed along the longitudinal axis and at least one laterally distal portion.

20. The disposable diaper of claim 2 wherein the absorbent assembly comprises an absorbent core comprising particles of superabsorbent polymer that are contained inside pockets formed by a thermoplastic material.

21. The disposable diaper of claim 2 wherein the absorbent assembly comprises a topsheet smaller in length than the web.

22. The disposable diaper of claim 2 wherein the absorbent assembly comprises an absorbent core comprising a layer of particles of superabsorbent polymer that are adhered to the absorbent core via adhesive.

23. The disposable diaper of claim 2 wherein the absorbent assembly comprises a first absorbent core comprising particles of superabsorbent polymer that are contained inside pockets formed by a thermoplastic material, and wherein the absorbent assembly comprises a second absorbent core comprising particles of superabsorbent polymer that are contained inside pockets formed by a thermoplastic material.

24. The disposable diaper of claim 23 wherein the pockets of the first absorbent core and the pockets of the second absorbent core are nested.

25. The disposable diaper of claim 2 wherein an inner liner is attached to the interior surface of the web.

26. The disposable diaper of claim 2 wherein the first side flap is attached to itself, interior surface to interior surface, in the front and back waist regions and wherein the second side flap is attached to itself, interior surface to interior surface, in the front and back waist regions.

27. The disposable diaper of claim 2 wherein the first side flap is attached to the absorbent assembly in the front and back waist regions and the second side flap is attached to the absorbent assembly in the front and back waist regions.

28. The disposable diaper of claim 2 wherein the web is a backsheet.

29. The disposable diaper of claim 28 wherein the backsheet is a single sheet.

30. The disposable diaper of claim 29 wherein the backsheet is vapor impermeable.

31. The disposable diaper of claim 30 wherein the backsheet is formed from polyethylene.

* * * * *

UNITED STATES PATENT AND TRADEMARK OFFICE
CERTIFICATE OF CORRECTION

| | | |
|---|---|---|
| PATENT NO. | : 7,736,351 B2 | Page 1 of 1 |
| APPLICATION NO. | : 10/770043 | |
| DATED | : June 15, 2010 | |
| INVENTOR(S) | : Nigam et al. | |

It is certified that error appears in the above-identified patent and that said Letters Patent is hereby corrected as shown below:

Title Page

References Cited

Page 3, column 1, line 69, delete "8,120,486" and insert --6,120,486--.

Signed and Sealed this
Seventeenth Day of January, 2012

David J. Kappos
*Director of the United States Patent and Trademark Office*